(12) United States Patent
Culver et al.

(10) Patent No.: US 7,459,290 B1
(45) Date of Patent: Dec. 2, 2008

(54) METHODS OF USING FUNCTIONAL 30S SUBUNITS

(75) Inventors: Gloria M. Culver, Ames, IA (US); Jennifer A. Maki, Hermantown, MN (US)

(73) Assignee: Iowa State University Research Foundation, Inc., Ames, IA (US)

( * ) Notice: Subject to any disclaimer, the term of this patent is extended or adjusted under 35 U.S.C. 154(b) by 222 days.

(21) Appl. No.: 11/094,770

(22) Filed: Mar. 30, 2005

Related U.S. Application Data

(60) Provisional application No. 60/557,606, filed on Mar. 30, 2004, provisional application No. 60/640,361, filed on Dec. 30, 2004.

(51) Int. Cl.
*C12P 21/06* (2006.01)
*C07H 21/04* (2006.01)
*C07H 21/02* (2006.01)

(52) U.S. Cl. ............... 435/69.1; 536/23.1; 530/300; 530/350

(58) Field of Classification Search ............ 435/69.1; 536/23.1; 530/300, 350
See application file for complete search history.

(56) References Cited

U.S. PATENT DOCUMENTS

| | | | |
|---|---|---|---|
| 4,440,676 | A | 4/1984 | Cadogan et al. |
| 4,867,976 | A | 9/1989 | Ueda et al. |
| 5,376,634 | A | 12/1994 | Iwamoto et al. |
| 5,478,730 | A | 12/1995 | Alakhov et al. |
| 5,502,033 | A | 3/1996 | Iwamoto et al. |
| 5,556,768 | A | 9/1996 | Yamashita |
| 5,556,769 | A | 9/1996 | Wu et al. |
| H1638 | H | 3/1997 | Furuta et al. |
| 5,643,744 | A | 7/1997 | Nitta et al. |
| 2002/0123101 | A1 | 9/2002 | Inoue et al. |
| 2003/0170811 | A1 | 9/2003 | Ueda et al. |

FOREIGN PATENT DOCUMENTS

| | | |
|---|---|---|
| EP | 0302442 A2 | 2/1989 |
| JP | 64-027493 | 1/1989 |
| JP | 4200390 | 7/1992 |
| WO | WO-88/08453 A1 | 11/1988 |

OTHER PUBLICATIONS

Alix, J.-H., et al., "DnaK-facilitated Ribosome Assembly in *Escherichia coli* Revisited", *RNA*, 9, (2003), 787-793.

Culver, G. M., et al., "Efficient Reconstitution of Functional *Escherichia coli* 30S Ribosomal Subunits From a Complete Set of Recombinant Small Subunit Ribosomal Proteins", *RNA*, 5, (1999), 832-843.

Culver, G. M., et al., "In Vitro Reconstitution of 30S Ribosomal Subunits Using Complete Set of Recombinant Proteins", *Methods in Enzymology*, vol. 318—RNA-Ligand Interactions (Part B), (2000), 446-460.

Green, R., et al., "In vitro Complementation Analysis Localizes 23S rRNA Posttranscriptional Modifications That Are Required for *Escherichia coli* 50S Ribosomal Subunit Assembly and Function", *RNA*, 2(10), (1996), 1011-1021.

Green, R., et al., "Reconstitution of Functional 50S Ribosomes From in Vitro Transcripts of *Bacillus stearothermophilus* 23S rRNA", *Biochemistry*, 38(6), (1999), 1772-1779.

Grondek, J. F., et al., "Assembly of the 30S Ribosomal Subunit: Positioning Ribosomal Protein S13 in the S7 Assembly Branch", *RNA*, 10, (2004), 1861-1866.

Held, W. A., et al., "Reconstitution of *Escherichia coli* 30 S Ribosomal Subunits from Purified Molecular Components", *The Journal of Biological Chemistry*, 248(16), (1973), 5720-5730.

Khaitovich, P., et al., "Peptidyl Transferase Activity Catalyzed by Protein-Free 23S Ribosomal RNA Remains Elusive", *RNA*, 5, (1999), 605-608.

Khaitovich, P., et al., "Reconstitution of Functionally Active *Thermus aquaticus* Large Ribosomal Subunits With in Vitro-Transcribed rRNA", *Biochemistry*, 38(6), (1999), 1780-1788.

Krzyzosiak, W., et al., "In Vitro Synthesis of 16S Ribosomal RNA Containing Single Base Changes and Assembly into a Functional. 30S Ribosome", *Biochemistry*, 26(8), (1987), 2353-2364.

Maki, J. A., et al., "Demonstration of the Role of the DnaK Chaperone System in Assembly of 30S Ribosomal Subunits Using a Purified in vitro System", *RNA*, 9, (2003), 1418-1421.

Maki, J. A., et al., "The DnaK Chaperone System Facilitates 30S Ribosomal Subunit Assembly", *Molecular Cell*, 10, (2002), 129-138.

Nierhaus, K. H., et al., "Ribosomal Proteins—XLIII. In vivo Assembly of *Escherichia coli* Ribosomal Proteins", *J. Mol. Biol.*, 74, (1973), 587-597.

Nierhaus, K. H., "The Assembly of Prokaryotic Ribosomes", *Biochimie*, 73, (1991), 739-755.

Nitta, I., "Possible Involvement of *Escherichia coli* 23S Ribosomal RNA in Peptide Bond Formation", *RNA*, 4, (1998), 257-267.

Southworth, D. R., et al., "EFG-Independent Translocation of the mRNA:tRNA Complex is Promoted by Modification of the Ribosome With Thiol-specific Reagents", *J. Mol. Biol.*, 324, (2002), 611-623.

*Primary Examiner*—Chih-Min Kam
(74) *Attorney, Agent, or Firm*—Schwegman, Lundberg & Woessner, P.A.

(57) ABSTRACT

A method of preparing a peptide in vitro in a defined translation mixture is provided. The method includes providing a defined translation reaction mixture comprising isolated and/or purified 30S subunits comprising small subunit ribosomal proteins and 16S rRNA, 50S subunits comprising large subunit ribosomal proteins, 5S rRNA and 23S rRNA, charged tRNAs for at least one amino acid, an isolated RNA template for translation with at least one codon corresponding to the anticodon in the charged tRNAs, and one or more isolated translation factors.

22 Claims, 5 Drawing Sheets

METHODS OF USING FUNCTIONAL 30S SUBUNITS

CROSS REFERENCE TO RELATED APPLICATIONS

This application claims the benefit of the filing date of U.S. application Ser. No. 60/640,361, filed Dec. 30, 2004, and U.S. application Ser. No. 60/557,606, filed Mar. 30, 2004, the disclosures of which are incorporated by reference herein.

STATEMENT OF GOVERNMENT RIGHTS

The invention was made, at least in part, with a grant from the Government of the United States (grant GM62432 and grant GM6243206 from the National Institutes of Health). The Government may have certain rights to the invention.

BACKGROUND OF THE INVENTION

Studies on the structure, function, and assembly of the *Escherichia coli* (*E. coli*) 30S ribosomal subunit were revolutionized when it was discovered that a mixture of the natural 30S ribosomal proteins (TP30) could be reconstituted with 16S ribosomal RNA (rRNA) into functional 30S subunits (Traub & Nomura, 1968). Subsequently, the individual protein components (S1-S21) of the 30S subunit were identified, purified, and characterized (Hardy et al., 1969; Nomura et al., 1969; Traut et al., 1969; Kaltschmidt & Wittmann, 1971). Individually purified ribosomal proteins added as a mixture could also be reconstituted with 16S rRNA into functional 30S subunits (Mizushima & Nomura, 1970; Held et al., 1974). The reconstituted 30S subunits were shown to have the same sedimentation behavior and protein composition as natural 30S subunits and were shown to function in tRNA binding and polyphenylalanine (polyPhe) synthesis. Taken together, these experiments demonstrated that 30S subunits are capable of self-assembly, and that all of the information required for in vitro assembly is contained within these molecular components.

While the ability to reconstitute *E. coli* 30S subunits in vitro from purified natural components allowed detailed investigation of the structure, function, and assembly of the 30S subunit, isolation of sufficient amounts of highly purified, functional small subunit ribosomal proteins from isolated subunits was difficult, laborious, and costly. In particular, it was difficult to exclude cross-contamination between ribosomal proteins in large-scale purification. Culver and Noller (1999) cloned and overexpressed a complete set of recombinant small subunit ribosomal proteins and developed an ordered assembly protocol that allowed efficient reconstitution of 30S subunits using the purified recombinant proteins. In particular, Culver and Noller (1999) found that reconstitution of 30S subunits with recombinant proteins was less efficient than those reconstituted using a complete mixture of natural ribosomal proteins (TP30) but more efficient than 30S subunit reconstitution using proteins individually purified from ribosomal subunits. The molecular composition and sedimentation properties of the recombinant 30S subunits were similar to those of natural 30S subunits and those reconstituted with TP30, and the recombinant 30S subunits were active, as measured by in vitro assays for tRNA$^{Phe}$ binding and polyPhe synthesis (Culver and Noller, 1999).

Based on in vitro reconstitution of functional 30S subunits using a mixture of total proteins isolated from the 30S subunit (TP30), individually purified natural (Held et al., 1973) or recombinant (Culver and Noller, 1999) small subunit proteins, and 16S rRNA, the association of 16S rRNA and various ribosomal proteins during 30S subunit formation was determined (FIG. 1A) (Mizushima and Nomura, 1970; Held et al., 1974). Some of the small subunit proteins, the primary binding proteins (1°; FIG. 1A), can bind independently and specifically to naked 16S rRNA. The secondary binding proteins (2°; FIG. 1A) require the prior association of at least one primary binding protein before they are able to interact appropriately with the growing RNP. Finally, the tertiary binding proteins (3°; FIG. 1A) bind once primary and secondary binding proteins have associated to complete the cooperative assembly of functional 30S subunits. Studies on the dynamics of in vitro 30S subunit assembly have shown that different regions of 16S rRNA undergo assembly at different rates (Powers et al., 1993), likely influenced by a combination of protein-dependent RNA conformational changes and rates of association of different proteins.

In vitro 30S subunit assembly is characterized by slow kinetics and is dependent upon optimal temperature and ionic conditions. At low temperatures, where *E. coli* growth is uncompromised, reconstitution stalls and a particle which sediments at 21S is formed (FIG. 1B) (Traub and Nomura, 1968). The 21S reconstitution intermediate (RI) contains a subset of the small subunit ribosomal proteins, corresponding to the primary and secondary proteins, and 16S rRNA (I; FIG. 1B) (Held and Nomura, 1973). A temperature-dependent conformational change is required to convert RI to an assembly competent intermediate, RI* which sediments at 26S (II; FIG. 1B). Once ΔRI* is formed, it is competent for assembly of the tertiary binding proteins (III; FIG. 1B). An intermediate similar to RI has been observed in vivo (Guthrie et al., 1969; Nashimoto et al., 1971; Nierhaus et al., 1973; Lindahl, 1975; Alix et al., 1993), strongly suggesting that in vitro and in vivo 30S subunit assembly follows similar paths.

Nevertheless, the observed in vitro and in vivo intermediates and the characteristics of in vitro 30S subunit reconstitution suggest that factors that normally assist 30S subunit assembly in vivo are lacking in the in vitro systems described above. Maki et al. (2002) identified components of the DnaK chaperone system that facilitated assembly of a functional 30S subunit from recombinant small subunit ribosomal proteins and 16S rRNA. However, Alix et al. (2003) disputed whether DnaK had a role in in vitro formation of functional 30S subunits.

Thus, it needs to be determined whether the DnaK chaperone system facilitates assembly of a functional 30S subunit.

SUMMARY OF THE INVENTION

The invention provides functional 30S subunits, functional 50S subunits, and 70S ribosomes prepared from isolated and/or purified 30S subunits and/or isolated and/or purified 50S subunits, as well as methods of making and using the isolated and/or purified 30S subunits and/or isolated and/or purified 50S subunits. In one embodiment, the invention provides a method to prepare a peptide. The method includes providing a defined translation reaction mixture comprising isolated and/or purified 30S subunits comprising small subunit ribosomal proteins and 16S rRNA, 50S subunits comprising large subunit ribosomal proteins, 5S rRNA and 23S rRNA, isolated charged tRNAs specific for at least one amino acid, an isolated RNA template for translation with at least one codon corresponding to the anticodon in the isolated charged tRNAs, and one or more isolated translation factors. The amounts of each component in the mixture are effective, after incubation, to yield a peptide encoded by the RNA template, e.g., a peptide having at least 2 amino acids and optionally at least 2 different amino acids. In one embodiment, the peptide is isolated from the translation mixture and optionally has an activity, e.g., binds a cellular molecule, e.g., DNA or a protein such as an antibody, or has enzymatic activity. In one embodiment, the isolated and/or purified 30S subunits have one or more recombinant small subunit ribosomal proteins and optionally are composed of only recombinant small subunit ribosomal proteins. In one embodiment, the 50S subunits are isolated and/or purified. The 50S subunits employed in the methods may have one or more recombinant large subunit ribosomal proteins and optionally are composed of only recombinant large subunit ribosomal proteins. The 30S and 50S subunits may include natural rRNA or recombinant rRNA. The 30S and 50S subunits may be prepared by any means, e.g., isolation from cells ("natural" subunits), or assembly in vitro, e.g., the 30S subunits may be prepared by contacting 16S rRNA with a first subset of small subunit ribosomal proteins to form a first ribonucleoprotein complex, and then the first ribonucleoprotein complex is contacted with a second subset of small subunit ribosomal proteins and optionally one or more accessory proteins to form a second ribonucleoprotein complex. In one embodiment, the second ribonucleoprotein complex is contacted with a third subset of small subunit ribosomal proteins. The ribosomal proteins employed in assembly may be natural proteins, i.e., one or more which are isolated from a nonrecombinant (wild-type) cell or a recombinant cell which does not recombinantly express one or more ribosomal proteins, i.e., "natural" ribosomal proteins, or recombinant proteins from a recombinant cell which expresses one or more ribosomal proteins from an expression cassette, or an in vitro transcription/translation mixture, or may be a combination of natural and recombinant proteins. The assembly may be conducted at a permissive or nonpermissive temperature, and in the presence or absence of nonribosomal proteins which facilitate assembly, i.e., accessory proteins including at least one of DnaK, DnaJ or GrpE. The accessory protein may be a natural protein, i.e., one which is isolated from a wild-type cell or a recombinant cell which does not recombinantly express the accessory protein, or from a recombinant cell which expresses the accessory protein from an expression cassette or an in vitro transcription/translation mixture. The defined translation mixture may include a translation factor such as EF-G or EF-T, and GTP, phosphoenolpyruvate or pyruvate kinase. In one embodiment, the translation factor is an isolated and/or purified translation factor.

Also provided is an isolated and/or purified functional 30S subunit comprising small subunit ribosomal proteins, and natural or recombinant 16S rRNA. In one embodiment, the isolated and/or purified 30S subunits are formed in the presence of chaperones under otherwise non-permissive conditions, and are highly similar to 30S subunits formed under standard reconstitution conditions. The manner in which the "factor-assembled" 30S subunits are purified can be correlated to the yield and efficiency of functional ribosomal particles. As described hereinbelow, sucrose gradient purification is one in vitro method to prepare 30S subunits of the invention, although other methods may be used to isolate and/or purify 30S subunits. For example, one or more recombinant ribosomal proteins may contain a tag useful to isolate and/or purify a ribosomal subunit, e.g., one or more of the peripheral ribosomal proteins that are added late in assembly, and optionally positioned away from the active site, may be used to isolate or purify subunits, e.g., for 30S subunits, S2 and/or S3 tagged with a HA tag and/or six His tag may be employed. Another in vitro method to prepare 30S subunits of the invention is via the use of a tRNA binding column.

Thus, 30S subunits of the invention may include natural or recombinant 16S rRNA. While generally lower recoveries of ribosomal subunits are obtained in assembly reactions with recombinant rRNA, the use of recombinant rRNA with recombinant ribosomal proteins to prepare ribosomal subunits provides for totally cell-free ribosomes. Moreover, the use of mutant recombinant rRNA in an assembly reaction may be useful to identify nucleotide residue(s) that alter fidelity, assembly rates, and/or translation rates.

To detect or determine the yield (recovery rate) and/or function of 30S subunits, a preferred assay is a tRNA binding assay, due to the fidelity of the base pairing that occurs on the 30S subunit between mRNA and tRNA. In contrast to the use of ribosomal proteins to prepare 30S subunits by the ordered assembly pathway (Culver et al., 1999), which provided for 30S subunit recovery rates of 45% and tRNA binding rates of about 48%, the methods described herein yield 30S subunits with recovery rates of about 65 to 70% or more, e.g., 75%, 80% or more, and tRNA binding rates of about 70% or more, e.g., 75%, 80%, 90% or more.

The isolated and/or purified 30S subunit of the invention, when combined with a 50S subunit, charged tRNAs specific for at least one amino acid, a RNA template with at least one codon corresponding to the anticodon in the charged tRNAs and one or more translation factors, is functional and so yields a peptide encoded by the RNA template. In one embodiment, the isolated and purified 30S subunit is prepared by contacting 16S rRNA with a first subset of small subunit ribosomal proteins to form a first ribonucleoprotein complex, and then the first ribonucleoprotein complex is contacted with a second subset of small subunit ribosomal proteins and optionally one or more accessory proteins to form a second ribonucleoprotein complex.

Further provided is a method to identify one or more nonribosomal proteins which enhance ribosomal subunit assembly. The method includes contacting a ribosomal subunit assembly reaction comprising a plurality of 30S or 50S ribosomal proteins and ribosomal RNA with one or more isolated nonribosomal proteins or a cell extract. Then it is determined whether one or more isolated nonribosomal proteins or a nonribosomal protein in the cell extract enhances ribosomal subunit assembly, and optionally the nonribosomal protein which enhances assembly is identified, wherein the nonribosomal protein is not DnaK, GrpE or DnaJ. In one embodiment, the assembly reaction lacks at least one ribosomal protein. In one embodiment, the assembly reaction, prior to contact with the one or more isolated nonribosomal protein or cell extract, comprises reconstitution intermediates and/or activated reconstitution intermediates.

Also provided is an isolated and/or purified 30S subunit comprising small subunit ribosomal proteins and 16S rRNA, wherein at least one of the ribosomal proteins comprises a tag. The tag is molecule which is capable of binding to another molecule, e.g., it is an affinity tag, and so is useful to isolate or purify the ribosomal protein having the tag or ribonucleoprotein complexes, e.g., a ribosomal subunit or ribosome, associated with the ribosomal protein having the tag. Further provided is a method to isolate ribosomes or subunits thereof. The method includes preparing a ribosome or a subunit thereof in vitro, wherein at least one of the ribosomal proteins comprises a tag. The in vitro prepared ribosome or subunit is contacted with a molecule that binds the tag so as to isolate the ribosome or subunit.

The invention also provides a method to purify functional ribosomes. The method includes providing a ribosome prepared in vitro and contacting the in vitro prepared ribosome with tRNA bound to a solid support so as to purify a func-

DETAILED DESCRIPTION OF THE INVENTION

Definitions

Figure 1A:
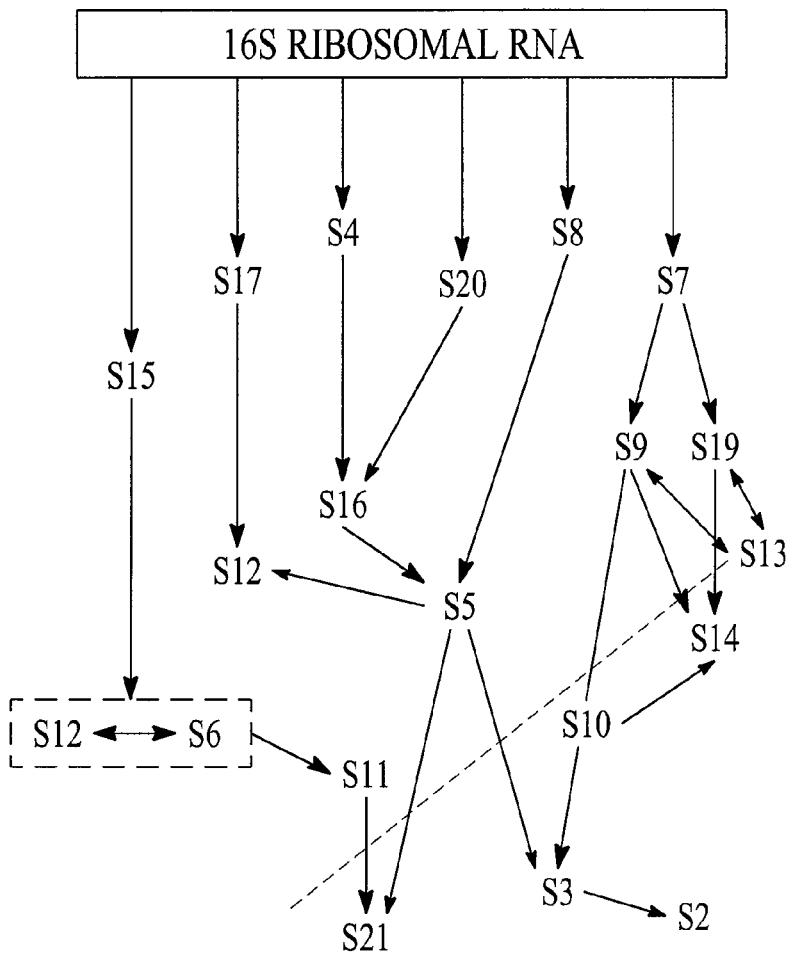
FIG. 1. In vitro assembly of E. coli 30S ribosomal subunits. (A) 16S rRNA is represented as a rectangle. Arrows indicate interactions between components. Primary (1°) binding proteins are black, secondary (2°) binding proteins are pink, and tertiary (3°) binding proteins are blue. S6 and S18 are shown in a dashed line box to indicate that they bind as a heterodimer. The dotted line indicates the separation of proteins found on the reconstitution intermediate (RI, above the line) from those that are added after activation (below the line). (B) Schematic path for in vitro 30S subunit assembly. RI, reconstitution intermediate. RI*, activated reconstitution intermediate. I designates incubation at low temperature. Δ and II designate heat activation at 42° C. III designates incubation at either low or high temperature.
Figure 1B:
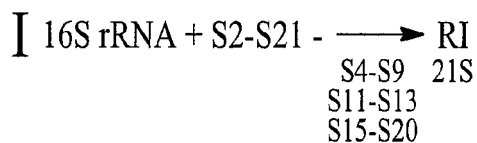
Figure 1B:
Figure 1B:
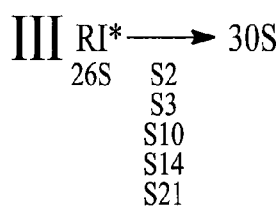

As used herein, "purified" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species. A 30S subunit which is subjected to sucrose gradient sedimentation or an affinity column, e.g., a tRNA column or other molecule which binds a 30S subunit, and washed and/or further concentrated, e.g., via a molecular sieving filter, is "purified" from other macromolecular species.

As used herein, "isolated" when used in relation to a nucleic acid, peptide, polypeptide or complex of peptides or polypeptides and nucleic acid, e.g., a ribonucleoprotein (RNP) complex, refers to a nucleic acid sequence, peptide, polypeptide or complex that is identified and separated from at least one contaminant nucleic acid, polypeptide, RNP or other biological component with which it is ordinarily associated in its natural source. Isolated nucleic acid, peptide, polypeptide or RNP is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins; and proteins and RNPs are found in the cell as a mixture with other cellular components. The isolated nucleic acid molecule may be present in single-stranded or double-stranded form. When an isolated nucleic acid molecule is to be utilized to express a protein, the molecule will contain at a minimum the sense or coding strand (i.e., the molecule may be single-stranded), but may contain both the sense and anti-sense strands (i.e., the molecule may be double-stranded). When isolated RNA is to be utilized as mRNA, the RNA is single-stranded and will contain at a minimum sequences specifically recognized and bound by a ribosome so as to initiate translation. For instance, a 30S subunit which is subjected to sucrose gradient sedimentation, an affinity column, e.g., a tRNA or other affinity column, or gel electrophoresis, or any combination thereof, is "isolated" from other cellular components.

A "functional" 30S subunit is one which specifically associates with a 50S subunit, specifically binds tRNA and/or when associated with a 50S subunit and other factors for translation, e.g., charged tRNAs, an RNA template, and translation factors, participates in peptide bond formation.

The term "recombinant nucleic acid molecule" as used herein refers to a nucleic acid molecule, including RNA, DNA or chimeras thereof, that is comprised of segments of nucleic acid joined together by means of molecular biological techniques.

The term "recombinant protein," "recombinant peptide" or "recombinant polypeptide" as used herein refers to a peptide or protein molecule that is expressed from a recombinant nucleic molecule.

"Natural" as used herein refers to a gene, gene product, e.g., rRNA, or complex of molecules, e.g., a RNP, that has the characteristics of that gene, gene product or complex when isolated from a cell or tissue.

"Permissive" as used herein is a temperature of 20° C. or greater which permits ribosomal subunit assembly in the absence of accessory proteins.

"Nonpermissive" as used herein is a temperature below 20° C.

"Accessory proteins" as used herein includes one or more nonribosomal proteins which enhance ribosomal subunit assembly in vitro relative to assembly in the absence of that protein.

A "peptide" as used herein includes two or more amino acids linked by a peptide bond.

As used herein, a "defined" translation reaction mixture does not include cellular extracts, e.g., S100 or S150 extracts.

Methods of Preparing Ribosomal Proteins, Accessory Proteins and Ribosomal RNAs for Subunit Assembly The ribosome is responsible for catalyzing the conversion of genetic information into functional proteins. All ribosomes are composed of two asymmetric subunits, each of which performs independent, fundamental roles that must be coordinated for cell viability. The small, 30S, subunit of the E. coli ribosome is composed of 16S rRNA and 21 proteins. These purified components are capable of assembling into functional 30S subunits in vitro (Nomura et al., 1969; Nomura et al., 1970; Nierhaus et al., 1974) in the absence of other factors, under certain conditions (permissive conditions). While in vitro 30S subunit assembly is thought to mirror in vivo assembly, the slow kinetics and sharp temperature dependence suggest that additional factors ("accessory factors") are involved in vivo (Alix et al., 1993; Bylund et al., 1998; Dammel et al., 1993; Dammel et al., 1965; El Hage et al., 2001; Inoul et al., 2003; Jones et al., 1996; Ruggen et al., 1998; Sbai et al., 1998; Toone et al., 1991; Xia et al., 1993). Potential roles for such factors include participation in protein and RNA folding and modification of these same components. The large or 50S subunit is composed of over 30 proteins, not all unique, and two RNAs, 5S (120 nucleotides) and 23S (2904 nucleotides). Each of these subunits performs discrete essential functions; the 30S subunit binds messenger RNA (mRNA) and actively participates in transfer RNA (tRNA) selection. Thus, the small subunit is largely responsible for maintaining translational accuracy and fidelity. The 50S subunit catalyzes peptide bond formation and thus is the catalytic center of the ribosome. The activities of these two subunits must be coordinated for accurate translation to occur.

To assemble 30S and/or 50S subunits in vitro, 16S rRNA, S5 rRNA and 23S rRNA may be isolated from cells ("natural" rRNA), or prepared recombinantly (Krzyzosiak et al., 1987; Green et al., 1996; Khaitovich et al., 1999; Green et al., 1999). Individual ribosomal proteins for subunit assembly may be isolated from wild-type cells ("natural" protein) or from recombinant cells, e.g., those that recombinantly express one or more ribosomal proteins or from in vitro transcription/translation mixtures ("recombinant protein"), or prepared via chemical synthesis. Accessory proteins for ribosomal subunit assembly/reconstitution likewise may be isolated or prepared. For instance, accessory proteins for prokaryotic ribosomal subunit assembly may be isolated from a post-ribosomal E. coli S100 or S150 extract. Preparation of an S100 extract involves lysis of E. coli in a French Press, centrifugation to obtain S100 and then adsorption of this supernatant to a DEAE-cellulose matrix (DE52) followed by discontinuous elution by a step gradient. Higher levels of purification may be achieved by using an open column format with a linear elution profile in place of batch binding and step elution. The protein concentration and content during the purification is monitored by both Bradford protein assays and SDS-polyacrylamide gel electrophoresis followed by Coomassie blue staining or to silver staining.

The ability to overcome a stall during in vitro reconstitution of 30S subunits may be employed as an assay for extra-ribosomal assembly factors. At low temperatures, a specific 16S rRNA-containing intermediate, which sediments at 21S, is formed during in vitro reconstitution. Sucrose gradient sedimentation analysis may be used to monitor the extract-dependent conversion of the 21S intermediate to 30S subunits at low temperatures. This assay is extremely sensitive and also allows the assembly process to be directly monitored. Additionally, the ability of the formed 30S subunits to function in subunit association can also be readily addressed using this technique.

One alternate approach is the use of low concentrations non-denaturing acrylamide or composite (low concentration acrylamide and agarose) gels to effectively separate ribosomal RNAs ranging from 16S to 23S (including processing intermediates), RI/21S assembly intermediates, activated RI*/26S assembly intermediates, 30S subunits and 70S ribosomes. The RNA can be detected by staining with methylene blue, allowing as little as 10 picomoles of RNA to be observed in a single species; alternatively, ethidium bromide staining can be used for increased efficiency of detection. The advantage of using 21S conversion to 70S ribosomes is two-fold. First, the size difference between 21S and 70S particles allows greater separation. Second, by assaying for 70S formation, a functional test on the 30S subunits that are formed in the presence of the assembly factor is imposed. Also, the reconstitution reactions can be loaded directly onto the gels allowing for much more rapid screening of samples and potentially limit artifacts due to manipulation.

Assembly can also be monitored by following the association of one (or more) of proteins (Group III in Table 1) that have never been found associated with the 21S intermediate and only join the growing RNP at the later stages of assembly, i.e., bind to the growing RNP only after the rate-limiting conformation change has occurred, by Western blotting. This approach is rapid and allows a greater number of fractions to be analyzed at each step of the purification than sucrose gradient sedimentation. Also, with sensitivity of some Western blot detection reagents (detection of as low as 5 pg of material), this approach allows low levels of 30S subunit formation to be detected. Indeed, this assay could be used in conjunction with sucrose gradient sedimentation to confirm that the peak fractions as identified by Western blotting correspond to fractions that actively convert 21S to 30S particles and thus confirm that the correct fractions had been carried into further rounds of purification.

The ability of the identified assembly activity to promote additional assembly events, as well as with other stalls in 30S subunit assembly, and with the ability to promote 50S subunit assembly, is tested. These experiments address whether the identified factor acts specifically at the RI to RI* transition of the 30S subunit or if it plays a more general role as a chaperone.

In vitro reconstitution of 30S subunits using a complete set of recombinant small subunit ribosomal proteins requires an ordered addition of the ribosomal proteins, as described for recombinant small ribosomal proteins in detail below in Example I. This reconstitution requirement is unique to the recombinant proteins and is not observed with natural proteins. To determine if an assembly factor can alleviate the ordered assembly requirement of recombinant proteins, 30S subunit reconstitution is monitored using the recombinant proteins and a one-step reconstitution procedure to address whether the factor is involved in general stimulation of assembly and capable of resolving a variety of stalled assembly complexes or if the factor performs a highly specific role in the conformational change from RI to RI*. These reconstitutions can be analyzed by sucrose gradient sedimentation or non-denaturing polyacrylamide gel electrophoresis. If the identified factor is capable of resolving the deficiency of the recombinant proteins, then a general chaperone has been identified that is involved in 30S ribosomal subunit assembly.

In vitro reconstitution of $E.\ coli$ 50S subunits is a multi-step reaction (Nierhaus et al., 1974; see Table 1). A shift in $MgCl_2$ concentration and in temperature are both required for efficient reconstitution (Nierhaus et al., 1974).

reaction conditions are as follows:

(23S+5S)rRNA+TP50–[4 mM $Mg^{2+}$,44° C.,20 minutes]–

–[20 mM $Mg^{2+}$,50° C.,90 minutes]→50S

A distinct particle is present already at 0° C., $RI_{50}(1)$, which disappears during incubation while a second distinct particle, $RI_{50}*(1)$, increases and then also slowly disappears while a third particle, $RI_{50}(2)$, appears at the same rate. When the relative amounts of the three reconstitution particles are drawn together with the activity monitored in a poly(U) dependent poly(Phe) reaction it becomes evident that the formation of the second particle, $RI_{50}*(1)$, is paralleled by the appearance of activity after the two-step incubation. Thus, the second particle is the essential product of the first-step incubation. The protein content of the precursor and reconstitution intermediates of the 50S subunit are shown in Table II.

TABLE II

Protein content of precursor particles and reconstitution intermediates of the 50S subunit from $E.\ coli$ ribosomes. L8 is the pentamer $L10(L7/L12)_4$; L26 is 30S protein S20.

| Protein | $p_1 50S^+$ | $p_2 50S^+$ | $RI_{50}(1)$ |
|---------|------------|------------|--------------|
| L1      | +          | +          | +            |
| L2      | –          | –          | (+)          |
| L3      | +          | +          | +            |
| L4      | +          | +          | +            |
| L5      | +          | +          | +            |
| L6      | –          | –          | –            |
| L7/L12  | ±          | +          | +            |
| L9      | +          | +          | +            |
| L10     | +          | +          | +            |
| L11     | ±          | +          | +            |
| L13     | +          | +          | (+)          |
| L14     | –          | +          | –            |
| L15     | –          | +          | +            |
| L16     | –          | –          | –            |
| L17     | +          | +          | +            |
| L18     | +          | +          | (+)          |
| L19     | –          | +          | –            |
| L20     | +          | +          | +            |
| L21     | +          | +          | +            |
| L22     | +          | +          | +            |
| L23     | +          | +          | +            |
| L24     | +          | +          | +            |

TABLE I

| Subunit | Step | rRNA (RI) | Proteins | Temp (mM $Mg^{2+}$) | Reconst interm (RI) | Sediment coefficient |
|---------|------|-----------|----------|---------------------|---------------------|----------------------|
| Large subunit | 1 | 23S + 5S | + L1, L2, L3, L4, L5, L7/L12, L9, L10, L11, L13, L15, L17, L18, L20, L21, L22, L23, L24, L26, L29, L33, L34 | 0° C. | $RI_{50}(1)$ | 33S |
|  | 2 | $RI_{50}(1)$ |  | 44° C. | $RI_{50}*(1)$ | 41S |
|  | 3 | $RI_{50}*(1)$ | + L6, L14, L16, L19, L25, L27, L28, L30, L31, L32 | 44° C. / 50° C. | $RI_{50}*(2)$ | 48S |
|  | 4 | $RI_{50}(2)$ |  | 50° C. | 50S |  |

TABLE II-continued

Protein content of precursor particles and reconstitution
intermediates of the 50S subunit from E. coli ribosomes.
L8 is the pentamer L10(L7/L12)$_4$; L26 is 30S protein S20.

| Protein | p$_1$50S$^+$ | p$_2$50S$^+$ | RI$_{50}$(1) |
|---------|------|------|--------|
| L25 | + | + | − |
| L27 | + | + | − |
| L28 | − | − | − |
| L29 | + | + | + |
| L30 | + | + | − |
| L31 | − | − | − |
| L32 | − | − | − |
| L33 | − | + | (+) |

$^+$p = precursors found in vivo; p$_1$50S sediments at 32S while p$_2$50S sediments at 43S It appears that the rate-limiting step of the first incubation is the conformational change RI$_{50}$(1)→RI$_{50}$*(1), and that of the second incubation is the conformational change RI$_{50}$(2)→50S (Table I). The activation energy of the rate-limiting reaction of the first step is sensitive to the preparation methods of both rRNA (Sieber et al., 1978) and TP50 (Herold et al., 1980), in contrast to that of the second step.

An assembly-initiator protein is a ribosomal protein which binds without cooperativity to an rRNA molecule and is essential for the formation of an active ribosomal subunit. Only those rRNA molecules with a complete set of initiator proteins are able to perform a correct assembly thus forming active particles.

The transition of the reconstitution intermediate RI$_{50}$(1)→RI$_{50}$*(1) is marked by a shift in S value from 33S to 41S (Table I). RI$_{50}$*(1) is the essential product of the early assembly during the first-step incubation which cannot be by-passed during the second step. Both intermediate particles consist of 23S and 5S rRNA and 20 different proteins. Only 23S rRNA and five proteins (L4, L13, L20, L22 and L24) were necessary and sufficient for establishing RI$_{50}$*(1), although L3 stimulated its formation (Merhas, 1991).

L15 and L16 are late-assembly components which play a decisive role in the organization of late assembly process, regardless of whether or not they are in addition important for stabilization of the structure and/or participate directly in ribosomal functions. However, ribosomes lacking either L15 or L16 or even both proteins can be reconstituted and are active in poly(U) dependent poly(Phe) synthesis. Either protein accelerates the assembly process by a factor of 2 to 4; the proteins act synergistically since both proteins together increase the assembly rate by a factor of 20.

5S rRNA is a late assembly component, as it can be added after the two-step reconstitution to a third incubation (Dohme et al., 1976). The activation effect of 5S rRNA is heat dependent, i.e., it induces a conformational change. However, in contrast to L15 and L16, fully active particles without 5S rRNA cannot be reconstituted. Moreover, in the presence of some antibiotics, 5S rRNA can be omitted from the reconstitution-reaction and appreciable activity detected (Khaitovich et al., 1999).

The order of pathways seems to be less rigid during the late assembly. Under standard reconstitution conditions the integration of L16 depends largely on the preceding incorporation of L15 (Rohl et al., 1982). However, a slight change in the ionic conditions (240 instead of 400 mM NH$_4$Cl) allows the L16 incorporation independent of L15 (Franceshi et al., 1998).

Ribosomal proteins which accelerate assembly, e.g., S16 (Held et al., 1975) and L15 (Franceshi et al., 1998), represent one class of assembly proteins. A second class of assembly proteins consists of proteins which are essential for achieving a distinct assembly stage which is a necessary intermediate in the path towards an active subunit, e.g., L20, L24, and L16 belong to this class. L20, L24 and other proteins are essential for the formation of the RI$_{50}$*(1) conformation, but if this conformation has been achieved, at least L20 and L24 can be again removed without losing the RI$_{50}$*(1) conformation. There are similar proteins that have been identified for the formation of RI* in 30S assembly, e.g., S4, S7, S8, S16 and S19 are all important for formation of the activated intermediate (Held et al., 1973). In addition, S3 and to a lesser extent S14 have been shown to be important for assembly but can be removed without a large change in 30S subunit function (Ramakrishnan et al., 1986).

The assembly of the 50S subunit may also be enhanced by an assembly factor. Initially, it is determined if an assembly factor can relieve either or both of the required shifts during 50S subunit reconstitution by monitoring 50S subunit formation using sucrose gradient sedimentation or native polyacrylamide gel electrophoresis. If the identified ribosome assembly factor has an effect on both 30S and 50S subunit assembly, a general ribosome assembly factor has been identified.

Natural 16S rRNA isolated from 30S subunits (Moazed et al., 1986) or recombinant 16S rRNA may be used in 30S reconstitutions, and natural or recombinant 5S rRNA and/or 23S rRNA may be used in 50S reconstitutions. For instance, 30S assay reactions with natural 16S rRNA are performed under standard reconstitution conditions (80 mM K$^+$-Hepes, 20 mM MgCl$_2$, 330 mM KCl, 0.01% Nikkol and 6 mM BME) using different combinations of the recombinant proteins. The recombinant proteins are generally added in molar excess over 16S rRNA to drive all of the RNA into particles. A peak that sediments at 21S in sucrose gradients is observed when Groups I and II are added to 16S rRNA following the ordered assembly protocol. In addition, a discrete peak is observed when only Group I is added to 16S rRNA. These particles are prepared by addition of Group I and by addition of Group I followed by Group II. Also, Group I and II are added simultaneously to determine if ordered assembly is required for production of this observed intermediate. Analogous experiments are performed using the protein groupings as determined from the kinetic studies (see Table 1).

Sucrose gradient sedimentation analysis may be used as the initial assay for specific complex formation. This approach can detect particles and is a means for isolating the specific particles. Particles can be isolated from the sucrose gradients by removal of sucrose and concentration of the sample by centrifugation through Centricon 30, 50 or 100 Ultraconcentrators (Amicon) at 4° C.; low temperature is used to promote stability of the RNPs. The particles are retained above the filter while sucrose passes through the filter. Multiple washes (purification) with reconstitution buffer insures that all the sucrose is removed (and therefore will not interfere with subsequent analysis). Reconstituted 30S subunits prepared in this manner are similar to natural 30S subunits. They have a full protein complement (as determined by 2-D gel electrophoresis), normal rRNA fold (as determined by chemical modification and primer extension analysis), are functional (as determined by tRNA binding and/or polyphenylalanine synthesis) and post-isolation still sediment at 30S, as determined by sucrose gradient sedimentation analysis. Sucrose gradient sedimentation post-isolation can determine whether the particles have degraded, unfolded or lost components during isolation.

The invention will be further described by the following non-limiting examples.

EXAMPLE I

Methods to Prepare Functional 30S Subunits from Recombinant Ribosomal Proteins Materials and Methods Preparation of 16S rRNA, 30S, 50S, and 70S ribosomes was as described in Moazed et al. (1986). Preparation of TP30 was as described in Nierhaus (1990). tRNA$^{Phe}$ was transcribed from p67CF10 (Sampson et al., 1989) as described in Milligan et al. (1987). Purification of individual ribosomal proteins from subunits was as described in Stem et al. (1988). Buffer A consisted of 80 mM K$^+$-HEPES (pH 7.6), 20 mM MgCl$_2$, 330 mM KCl, and 0.01% Nikkol. Buffer B consisted of 20 mM Tris-HCl (pH 7.0), 20 mM KCl, 6 M urea, and 6 mM β-mercaptoethanol (BME). Buffer C consisted of 20 mM NaOAc (pH 5.6), 20 mM KCl, 6 M urea, and 6 mM BME. Buffer D consisted of 80 mM K$^+$-HEPES (pH 7.6), 20 mM MgCl$_2$, 1 M KCl, and 6 mM BME. Buffer E consisted of 20 mM K$^+$-HEPES (7.6), 20 mM KCl, and 6 mM BME.

Cloning Genes Encoding Ribosomal Proteins S2-S21

The genes encoding S5 and S17 were previously cloned (Heilek & Noller, 1996b). The genes encoding ribosomal proteins S2-S4, S6-S16, and S18-S21 were amplified by polymerase chain reaction (PCR) of E. coli MRE600 genomic DNA. An NdeI restriction enzyme site was included at the 5' end of every clone. Either a BamHI (S2-S4, S6, S8-S16, S18, S19, and S21) or a HindIII (S7 and S20) restriction enzyme site was included at the 3' end of the genes. The PCR products were cleaved with the appropriate enzymes (see above) and ligated into pET24b that had been cleaved with the same enzymes and purified. Wild-type clones were identified by sequence analysis and transformed into BL21 (DE3), where the proteins were overexpressed from an inducible T7 promoter on the plasmid (Studier et al., 1990; Novagen). For overexpression, strains harboring the plasmids were grown to an approximate OD$_{600}$ of 0.4, IPTG was added to a final concentration of 1 mM, and the cultures were grown for an additional 4 hours prior to harvesting. Cells were washed once with Buffer E and stored at −20° C. For analysis of overexpression, equal volumes of induced cell culture and SDS-PAGE loading dye containing 6 M urea were mixed, and 30 μL of the resulting mixture was analyzed by SDS-polyacrylamide gel electrophoresis (Laemmli, 1970; 4% stacking gel; 12% resolving gel, both containing 6 M urea).

Purification of Recombinant Ribosomal Proteins S2-S21

Cells containing overexpressed protein were disrupted by sonication at 4° C. in Buffer E. Postsonication centrifugation at 4° C. either cleared the protein-containing lysate or pelleted the protein-containing inclusion bodies. Inclusion body pellets containing overexpressed protein were resuspended in Buffer B (S3, S5, S8, S9, S11, S18, and S21) or Buffer C(S2, S6, and S17) and dialyzed overnight against two changes of the same buffer at 4° C. Soluble proteins were dialyzed overnight at 4° C. against three changes of Buffer B (S4, S7, S12-S16, S19, and S20) or Buffer C(S10). Proteins (S2-S5, S7-S21) were purified at 4° C. by FPLC cation exchange chromatography using a Resource S column (Pharmacia) with 125 mL linear gradients (20-350 mM KCl) starting in dialysis buffer (B or C, as appropriate). Ribosomal protein S6 was purified at 4° C. by FPLC chromatography on a Resource Q anion exchange column (Pharmacia) developed in Buffer C with a 125 μL linear gradient from 20-350 mM KCl. Protein-containing fractions (5 μL) were identified by SDS-polyacrylamide electrophoresis (Laemmli, 1970; see above) and dialyzed against Buffer D, except for S10 and S18, which were dialyzed against Buffer D plus 4 M urea. Protein concentration was determined by Bradford assay (Bio-Rad). Aliquots of the proteins were frozen at −80° C.

Reconstitution and Purification of 30S Subunits

Prior to reconstitution, mixtures of pure recombinant proteins were prepared following either the 30S subunit assembly map (am; see Table III): Group I (am), containing equimolar amounts of S4, S7, S8, S15, S17, and S20; Group II (am), containing equimolar amounts of S5, S6, S9, S11, S12, S13, S16, S18, and S19; Group III, containing equimolar amounts of S2, S3, S10, S14, and S21; or following assembly kinetics (ak; see Table III): Group I (ak), S4, S6, S11, S15, S16, S17, S18, and S20; Group II (ak), S7, S8, S9, S13, and S19; Group II (ak), S5 and S12; Group III, same as above. These protein mixtures were concentrated on Microcon 3 microconcentrators at 4° C., and protein concentration determined by the Bradford assay. Protein mixtures were aliquoted and stored at −80° C. For experiments using proteins that were individually isolated from subunits, mixtures were prepared as described above following the assembly map. The salt concentration of the protein mixtures was maintained at 1 M KCl (Buffer D) to ensure that the proteins remained in solution. Since reconstitution proceeds at 330 mM KCl (Buffer A), the KCl concentration must be readjusted after addition of each mixture of proteins during reconstitution. Reconstitution of 30S particles was done using a 4-fold molar excess of each purified recombinant protein over 16S rRNA, following an ordered assembly protocol. In a standard reaction, 40 pmol of 16S rRNA were incubated in 5 μL of Buffer A minus KCl at 42° C. for 15 minutes. Group I proteins were added to 16S rRNA, the buffer conditions were adjusted to those of Buffer A, and the reaction was incubated at 42° C. for 20 minutes. Group II proteins were then added to the reconstitution reaction, buffer conditions were again adjusted to those of Buffer A, and the resulting reaction was again incubated at 42° C. for 20 minutes. Lastly, Group III proteins were added to the reaction, the KCl concentration adjusted to that of Buffer A in a final volume of 100 μL, and the reaction incubated at 42° C. for 20 minutes.

For reconstitution using the assembly kinetics groupings, the same procedure was followed except for an additional incubation with Group II' proteins, after the addition of Group II and prior to the addition of Group III. Reconstitution using TP30 was performed as described in Powers et al. (1993). Reconstitution of 30S subunits was analyzed by sucrose gradient sedimentation using 10-40% sucrose gradients in 20 mM K$^+$-HEPES (pH 7.6), 20 mM MgCl$_2$, and 330 mM KCl centrifuged in a SW41 rotor (32,000 rpm) for 15.5 hours at 4° C. Peaks sedimenting at 30S were isolated, and sucrose was removed from 30S subunits by centrifugation at 4° C. for 60 minutes at 2,400 rpm in Centricon 100 ultraconcentrators in a JA-20 rotor with three to four sequential 2 μL washes with Buffer A.

TABLE III

Subsets of proteins used for ordered reconstitution.

| Group | Assembly map[a] | Assembly kinetics[b] |
|---|---|---|
| I | S4 | S4 |
|   | S7 | S6 |
|   | S8 | S11 |
|   | S15 | S15 |
|   | S17 | S16 |
|   | S20 | S17 |

TABLE III-continued

Subsets of proteins used for ordered reconstitution.

| Group | Assembly map[a] | Assembly kinetics[b] |
|---|---|---|
|  |  | S18 |
|  |  | S20 |
| II | S5 | S7 |
|  | S6 | S8 |
|  | S9 | S9 |
|  | S11 | S13 |
|  | S12 | S19 |
|  | S13 |  |
|  | S16 |  |
|  | S18 |  |
|  | S19 |  |
| II |  | S5 |
|  |  | S12 |
| III | S2 | S2 |
|  | S3 | S3 |
|  | S10 | S10 |
|  | S14 | S14 |
|  | S21 | S21 |

[a]Based on Held et al. (1974) and Mizushima & Nomura (1970).
[b]Based on Powers et al. (1993).

Subunit Association of Reconstituted 30S Subunits and Natural 50S Subunits

In a standard reaction, unpurified reconstituted 30S subunits were incubated with 30 pmol natural 50S subunits in 80 mM K$^+$-HEPES (pH 7.6), 20 mM MgCl$_2$, 100 mM KCl, and 0.003% Nikkol at 37° C. for 30 minutes. Sucrose gradient sedimentation using 10-40% sucrose gradients in 20 mM K$^+$-HEPES (pH 7.6), 20 mM MgCl$_2$, and 100 mM KCl centrifuged in a SW41 rotor (32,000 rpm) for 15.5 hours at 4° C. was used to analyze subunit association.

Polyphenylalanine Synthesis

Polyphenylalanine synthesis was assayed essentially as described by Nomura and co-workers (Traub et al., 1981). Briefly, 10 pmol isolated 30S subunits and 10 pmol natural 50S subunits were incubated at 37° C. for 20 minutes. To the ribosomes, 100 pmol tRNA$^{Phe}$, 1.2 µL 0.5 µg/µL pyruvate kinase, 2.4 µL $^{14}$C-phenylalanine, 1 µM phenylalanine, 1 µL S100 extract, 9 µL polyphenylalanine buffer were added, the final volume adjusted to 30 µL with water, and incubated at 30° C. for 10 minutes. Poly(U) (8 µg) was added to initiate the reaction and the sample was incubated at 30° C. Reactions were stopped by spotting on Whatman filter paper at 0, 5, 10, and 20 minutes and filters were submerged in ice-cold 10% TCA after spotting. Filters were boiled twice in 5% TCA, washed with 95% ethanol, dried, and counted.

Transfer RNA Binding

Transfer RNA binding (Nirenberg & Leder, 1964) was performed as described in Moazed & Noller (1986) with slight modifications. Ribosomal particles (5 pmol) were incubated with 10 pmol [$^{32}$P]tRNAPhe (3'-end labeled with [$^{32}$P]-pCp) and 7.5 mg poly(U) in 50 µL 20 mM MgCl$_2$, 100 mM KCl, 80 mM K$^+$-HEPES (pH 7.6) for 15 minutes at 37° C. followed by 10 minutes on ice. Reactions were spotted on nitrocellulose filters, washed, and counted.

Two-Dimensional Protein Gel Electrophoresis

Proteins were extracted from 100 pmol of isolated 30S subunits as described in Siegmann & Thomas (1987). Two-dimensional protein gel electrophoresis of the recovered proteins was performed as described in Geyl et al. (1981).

Results

Cloning Expression, and Purification of Ribosomal Proteins S2-S21

Genomic DNA from *E. coli* MRE600 was used as a template for polymerase chain reaction (PCR) amplification of the genes encoding ribosomal proteins S2-S4, S6-S16, and S18-S21. The genes encoding S1 (Sorensen et al., 1998), S5 (Heilek & Noller, 1996b), and S17 were previously cloned. Primers for the PCR reactions were designed to facilitate cloning (by the inclusion of restriction enzyme sites) and expression (by optimizing the distance between the start codon and the ribosome binding site within the vector). After amplification and restriction enzyme digestion, the PCR products were cloned directly into the pET24b vector (Novagen), which contains an inducible promoter and an f1 origin for production of single-stranded DNA. The integrity of each individual clone was confirmed by restriction enzyme digestion and DNA sequence analysis. Induction of protein expression in the *E. Coli* strain BL21 (DE3) resulted in production of differing amounts of the various proteins of which some were soluble and some insoluble; the perceived differences in induction levels may in part have reflected varying staining efficiencies of the different proteins. The level of overexpression and the highly charged nature of most of the proteins enabled single-column FPLC purification. S2 had a relatively low isoelectric point (Kaltschmidt, 1971), was insoluble, and was purified at lower pH, compared to S4, which was quite basic, soluble, and purified at the higher of the two pHs used during chromatography (Kaltschmidt, 1971). Each of the overexpressed proteins was similarly purified to near homogeneity by FPLC cation-exchange chromatography, except for S6, which was purified by FPLC anion-exchange chromatography.

Reconstitution of 30S Subunits Using a Complete Set of Recombinant Proteins

Once purified, the recombinant proteins were assayed for their ability to support 30S subunit reconstitution with 16S rRNA by sucrose gradient sedimentation analysis. Natural 30S subunits and particles reconstituted using TP30 were used as controls for sedimentation and reconstitution. Following procedures of Nomura and coworkers (Traub & Nomura, 1969; Mizushima & Nomura, 1970), reconstitution using up to an eightfold excess of an equimolar mixture of the recombinant proteins over 16S rRNA resulted in very inefficient reconstitution.

To facilitate reconstitution, the results of earlier studies that mapped the pathway and order of in vitro protein assembly into 30S subunits were used as a guide to subdivide the proteins into three groups (Table III), based on their requirements for assembling on the growing RNP (Mizushima & Nomura, 1970; Held et al., 1974). Sequential addition of the recombinant proteins, using these groupings, and incubation with 16S rRNA resulted in efficient reconstitution. Note that more recent work (Grondek et al., 2004, the disclosure of which is incorporated by reference herein) links S13 to the 3' major domain and the S7 assembly branch, as S13 can bind to 16S rRNA in the presence of S7 but not S20.

Optimal reconstitution was observed using a 4-fold molar excess of protein to 16S rRNA. Approximately 45% of the input 16S rRNA was incorporated into 30S subunits following this procedure (Table IV); in contrast, when all the recombinant proteins were added in a single step only 18% of the input 16S rRNA was incorporated into 30S subunits.

TABLE IV

Recovery, tRNA binding, and polyphenylalanine synthesis of reconstituted 30S subunits.

| 30S | Recovery[a] (%) | tRNA Phe binding[b] poly (U)-dependent (% activity) | tRNA Phe binding[b] poly (U)-independent (% activity) | Polyphe synthesis[c] (% activity) |
|---|---|---|---|---|
| Natural[d] | | 100 ± 3 | 20 ± 4 | 100 ± 2 |
| TP30[e] | 70 | 72 ± 5 | 16 ± 3 | 79 ± 3 |
| Recombinant[f] | 45 | 48 ± 4 | 12 ± 3 | 34 ± 2 |

[a]Recovery is based on comparison of amount of input 16S rRNA to the amount of 30S subunits isolated and purified from sucrose gradients.
[b]For tRNA binding, 100% binding is equal to 0.7 pmol tRNA $^{Phe}$bound/pmol of 30S subunits.
[c]For polyphenylalanine synthesis, 100% activity is equal to 9.0 pmol of polyphenylalanine synthesized/pmol 30S subunits.
[d]Natural 30S subunits.
[e]30S subunits reconstituted with 16S rRNA and proteins isolated from 30S subunits.
[f]30S subunits reconstituted with 16S rRNA and a complete set of recombinant proteins.

An alternative ordered assembly protocol was tested, in which the proteins were divided into four groups, based on their order of assembly inferred from the kinetics of in vitro assembly monitored by chemical probing of 16S rRNA (Powers et al., 1993; Table III). Sequential addition of the recombinant proteins, following these groupings, also resulted in efficient reconstitution, with a similar protein:RNA optimum of 4:1. These data suggested that sequential addition of the recombinant proteins overcomes a kinetic barrier to reconstitution.

Functional Characterization of Recombinant Reconstituted Particles

The functional state of the recombinant reconstituted 30S particles was assessed by their ability to associate with 50S subunits, to bind tRNA and to participate in poly(U)-directed polyphenylalanine synthesis. Reconstituted unpurified 30S subunits, as well as control natural 30S subunits, were incubated with natural 50S subunits, and the formation of 70S ribosomes was monitored by sucrose gradient sedimentation. It was clear from the absence of material sedimenting at 30S that all of the 30S subunits were competent for association with 50S subunits. The lower yield of 70S ribosomes using the recombinant reconstitution system paralleled the lower yield of 30S subunits in reconstitution. Isolated and purified 30S subunits (natural, recombinant protein, and TP30) were assayed for their ability to bind tRNA using poly(U) as a template. Recombinant protein reconstituted 30S subunits were approximately 50% as active as natural 30S subunits in tRNA binding (Table IV). For comparison, 30S subunits reconstituted with TP30 showed intermediate activity, approximately 70% of that of natural 30S subunits (Table IV). The activity observed for 30S subunits reconstituted with recombinant proteins was comparable to that previously reported for 30S subunits reconstituted from proteins individually isolated from subunits (Table IV; Nomura et al., 1969). The residual poly(U)-independent binding was in the range of that expected under the $MgCl_2$ concentrations used in the reconstitutions and subsequent assays (Lill et al., 1986).

Lastly, the reconstituted 30S subunits were assayed for their ability to function in poly(U)-directed polyphenylalanine synthesis. In the presence of natural 50S subunits and cofactors, purified recombinant protein reconstituted 30S subunits supported polyphenylalanine synthesis with an activity, relative to natural 30S subunits, that was similar to that observed for tRNA binding (Table IV), and very similar to that previously reported for 30S subunits reconstituted from individually purified natural proteins (Nomura et al., 1969).

Discussion

Reconstitution of functional 30S subunits from a complete set of recombinant small subunit ribosomal proteins and 16S rRNA was efficient and was facilitated by addition of the ribosomal proteins in an ordered manner reflecting 30S subunit assembly. Sequential addition of the recombinant proteins using either the in vitro 30S subunit assembly map (Mizushima & Nomura, 1970; Held et al., 1974; Table III) or the results of in vitro 30S subunit assembly kinetics (Powers et al., 1993; Table III) resulted in efficient reconstitution (Table IV). The 16S rRNA in 30S subunits reconstituted with recombinant proteins had a DMS modification pattern indistinguishable from that of natural 30S subunits or subunits reconstituted from TP30. The protein composition of the recombinant 30S subunits is similar to that of natural 30S subunits and 30S subunits reconstituted from TP30. In addition, 30S subunits reconstituted with recombinant proteins function in subunit association, tRNA binding (Table IV), and polyphenylalanine synthesis (Table IV), although they were somewhat less active than either natural 30S subunits or 30S subunits reconstituted with TP30. This is in agreement with previous work that showed that 30S subunits reconstituted with proteins individually isolated from subunits also had lower activity than 30S subunits reconstituted with TP30 (Mizushima & Nomura, 1970). Thus, recombinant reconstituted 30S subunits are structurally and functionally very similar to subunits reconstituted with proteins isolated as a mixture from ribosomes and to natural 30S subunits.

Because reconstitution was optimal with a 4-fold molar excess of recombinant proteins to 16S rRNA for both groupings, as compared to a 1.8- to 2-fold molar excess of TP30 (Nomura et al., 1969), it is possible that, while one or more of the recombinant proteins are required in a larger amount, increased levels of the other recombinant proteins could contribute to nonproductive interactions when added en masse. Moreover, sequential addition of the proteins may reduce the interference of the excess protein with productive interactions.

The requirement for ordered addition of the recombinant proteins for efficient reconstitution could be due to a number of possible factors. Some of the small subunit ribosomal proteins are subject to posttranslational modification (Leibowitz & Soffer, 1971; Cumberlidge & Isono, 1979; Reeh & Pedersen, 1979; Isono & Isono, 1980; Kowalak & Walsh, 1996). Therefore, one or more of the overproduced, recombinant proteins might be substoichiometrically modified. Although all of the recombinant proteins were overexpressed in *E. coli* and thus available to their natural modification enzymes, the levels of expression may exceed the capacity of the endogenous enzymes. Ordered assembly could obviate the need for specific modifications; binding a subset of proteins to 16S rRNA could promote or increase the lifetime of transiently formed intermediates, thus allowing an inadequately modified protein, perhaps with a weakened binding affinity, the opportunity to interact productively with its target, prior to the addition of other proteins and subsequent conformational changes. Proteins that were isolated from ribosomes may be in a more functional conformation if prior ribosome assembly involves rearrangement of protein structure; therefore, it is possible that one or more of the recombinant proteins is incompletely folded as isolated, and that other proteins and/or RNA could stimulate their folding into a more functional conformation. Thus, ordered assembly could help this folding problem if incubating the incompletely folded protein with a subset of small subunit proteins or 16S rRNA potentiates folding. This could reflect the process that occurs in vivo, where a subset of proteins might initiate assembly cotranscriptionally. Either of the above possibilities could result in overestimation of the concentration of functional protein. The same would be true if a subpopulation of protein(s) were inactivated during purification, as was hypothesized for proteins isolated from ribosomes (Nomura et al., 1969).

This set of proteins will be of great use, not only in studying the proteins themselves but, also as tools for studying the structure. Along with the ability to purify tens of milligrams of recombinant ribosomal proteins with relative ease, the high levels of overexpression of these proteins can provide proteins that are essentially free of contamination with other ribosomal and cellular proteins.

EXAMPLE II

Methods to Identify Accessory Proteins in 30S Ribosomal Subunit Assembly

Materials and Methods

In Vitro Reconstitution, Gradient Fractionation, and Isolation/Purification of Particles In vitro reconstitution of 30S subunits, sucrose gradient sedimentation, purification and concentration of ribosomal particles, and protein analysis were performed essentially as described in Example I and Culver and Noller (2000). In all reconstitutions, the final concentration of 16S rRNA was 0.4 µM, that of each recombinant protein was 2.8 µM, and that of TP30 was 0.6 µM. Reconstitutions were performed at 15° C. with incubations at 42° C. designated by Δ. Reconstituted particles were concentrated using Centricon 100s (Amicon, Millipore Corp., Bedford, Mass.) except in one instance where Centricon 3s were used. For all sucrose gradient sedimentation experiments, top and bottom indicate sedimentation direction, and absorbance was monitored at 254 nm.

Reconstitutions using chaperones (and the corresponding controls) contained 100 µM ATP (final concentration) except in one instance where 100 µM ATPγS was used in place of ATP. Also, reconstitution reactions including chaperones (and the associated control reconstitutions) contained 10% glycerol (v/v, final concentration), 0.4 µM DnaK, 0.4 µM DnaJ, and 0.8 µM GrpE.

S100 Extract Preparation

S100 extract was prepared by resuspending 10 g of MRE600 $E.\ coli$ in 20 mM Tris-HCl (pH 7.5), 10 mM $MgCl_2$, 22 mM $NH_4Cl$, and 6 mM β-mercaptoethanol (BME). Cells were lysed by passing them through a French Press twice (12,000 psi). Cell lysate was cleared by centrifugation at 16,000 rpm (JA-20) at 4° C. The cell lysate was centrifuged at 33,000 rpm for 12 hours in a Ti-70 at 4° C. Supernatant was loaded onto a 40 ml DE52-cellulose column and washed with 400 ml of the extract buffer. The enzyme fraction was eluted with the same buffer except the $NH_4Cl$ concentration was 250 mM. Fractions were aliquoted and stored at −80° C.

Protein Sequence Analysis

Preparation of the Protein Sample for N-Terminal Sequence Analysis was performed essentially as described by Matsudaira (1987), and sequencing was performed by the Protein Facility at Iowa State University.

Western Analysis

Anti-DnaK, -GrpE, -DnaJ, and secondary antibodies were purchased from StressGen (Victoria, BC, Canada). Amersham-Pharmacia ECL Western blot analysis kit (Piscataway, N.J.) was used as described in company literature for analysis. Isolated and concentrated particles (see above, and Culver and Noller, 2000) were precipitated with 5 volumes of ice-cold acetone, and the resulting pellets were analyzed resulting in a nonquantitative loading.

Chaperone Components

Recombinant DnaK was produced and purified using an expression system based on the IMPACT system (New England Biolabs, Beverly, Mass.) provided by Anthony L. Fink and Charles Sargenti, University of California, Santa Cruz. Strain ER2566 containing DnaK cloned into pTYB1 was grown to an $OD_{550}$ of 0.6-0.8 in 2×YT at 37° C. Cultures were induced by addition of 1 mM IPTG (final concentration) and grown at 17° C. for 6 hours. Cells were harvested by centrifugation at 5,000 rpm for 10 minutes, washed once with Buffer K (20 mM $K^+$-Hepes, pH 7.6, and 330 mM KCl) and then stored at −80° C. Cells were disrupted by sonication in 6 ml of Buffer K at 4° C., and all subsequent steps were performed at 4° C. The resulting lysate was cleared by centrifugation for 15 minutes at 5,000 rpm. The supernatant was loaded on a 3 ml chitin column (New England Biolabs) that was previously equilibrated in Buffer K. The column was washed with 24 ml of Buffer K. DTT was added (final concentration of 40 mM), and the column was sealed and gently rocked overnight. The matrix was allowed to settle prior to elution of cleaved DnaK with 18 ml of Buffer K. Fractions containing DnaK were identified by SDS-PAGE analysis (Laemmli, 1970) and then stored at either 4° or −80° C. Protein concentration was determined by the Bradford assay. For reconstitutions, purified DnaK, GrpE, and DnaJ were purchased from StressGen.

Transfer RNA Binding

Transfer RNA binding was performed as described in Example I.

DnaK Affinity Chromatography

Affinity chromatography was performed following the general procedure of Kellogg and Alberts (1992). A DnaK affinity column matrix (1 ml) was prepared using a DnaK-intein-chitin fusion protein (see above). The DnaK fusion occurs at the very C-terminus of DnaK and is likely well enough removed from the active site to not interfere with substrate binding. An extract containing the DnaK-intein-chitin fusion protein (prepared as described above) was applied to a chitin binding domain matrix. Cellular proteins (which should not bind the matrix) were eluted by washing with 7 column volumes of Buffer K followed by 3 column volumes of Buffer K (low) (20 mM $K^+$-Hepes, pH 7.6, and 50 mM KCl). A mixture of a complete set of purified recombinant small subunit ribosomal proteins (6000 pmol total) was applied to the column matrix in Buffer K (low) and allowed to bind to the matrix as a batch overnight. The matrix was allowed to settle, and unbound proteins were removed in flow through and subsequent wash steps with Buffer K (low). Bound proteins were eluted in a series of steps with increasing KCl concentration from 100 mM to 1 M KCl. A final step cleaved DnaK from the column using 40 mM DTT to ensure that DnaK remained stably bound to the matrix throughout the procedure. SDS-PAGE analysis (see above) of the individual column fractions was performed after concentration by precipitation with 5 volumes of ice-cold acetone.

Bacterial Strains, Plasmids, and Growth Conditions

E. coli strain dnaK756 (originally groPC756) (Georgopoulos et al., 1973; Yochem et al., 1978) was obtained from the E. coli Genetic Stock Center (New Haven, Conn.). For expression in the dnaK756 background, the genes encoding S4, S8 and S15 were subcloned from previously prepared plasmids that contain the wild-type genes (Example I). Fragments (Ndel and EcoRl) containing the wild-type genes were ligated into the pALTER-1 vector (Promega, Madison, Wis.) digested with the same enzymes. Ligation reactions were transformed into XL-1 Blue Kanr cells (Stratagene, La Jolla, Calif.), and clones were confirmed to have the appropriate inserts. The pALTER vector, pALTER/S4, pALTER/S8, and pALTER/S15 DNAs were then transformed into dnaK756.

For the dilution plating, equal number of cells from overnight cultures grown in Luria Broth (LB)+10 µg/ml tetracycline (tet) at 37° C. were subcultured into low-salt broth (LSB; same as LB except ⅒ as much sodium chloride)+10 µg/ml tet+1 mM IPTG (final concentration) and grown at either 37° C. (permissive) or 43° C. (non-permissive) for 3.5 hours. 10-fold serial dilutions were made using LSB and were plated on LSB plates containing 10 µg/ml tet. Plates were incubated at 37° C. for 14 hours or at 42° C. for 60 hours. For doubling time calculations, cells were grown in liquid as described above except $OD_{600}$ measurements were made at various times. Cultures that were grown at 42° C. were induced with 1 mM IPTG (final concentration) at time zero while cultures that were grown at 37° C. were induced after 70 minutes.

Polysome Analysis

Polysomes were prepared based on standard protocols with some slight modifications. Briefly, equal number of cells from overnight cultures grown in LB+10 µg/ml tet at 37° C. were subcultured into LB or LSB containing 10 µg/ml tet and 1 mM IPTG (final concentration) and grown at either 37° C. (permissive) or 42° C. (nonpermissive) for 8.5 hours. $OD_{550}$ measurements were taken at this time. Cell cultures were rapidly chilled by pouring over ice. Cells were harvested by centrifugation at 10,000 rpm for 5 minutes at 4° C. Cell pellets were resuspended in 0.5 ml chilled lysis buffer (10 mM Tris-HCl, pH 7.8, 15 mM $MgCl_2$, 1 mg/ml lysozyme) and frozen in a dry ice/ethanol bath. Cells were thawed in an ice water bath, refrozen in a dry ice/ethanol bath, and then stored at −80° C. until needed. To finish cell lysis, cells were thawed in an ice water bath. 15 µl 10% deoxychloate was added to each sample, and the samples were centrifuged at 13,200 rpm for 20 minutes at 4° C. For polysomes that were prepared from cultures grown in LB, lysate from an equal number of cells was loaded on onto a 10%-40% sucrose gradient containing 20 mM Tris-HCl, pH 7.8, 10 mM $MgCl_2$, 100 mM $NH_4Cl$, and 2 mM DTT. Gradients were centrifuged in an SW-41 rotor for 3.5 hours at 35,000 rpm at 4° C. For polysomes prepared from cultures grown in LSB, a complete correction for different number of cells could not be made due to the lack of growth at 42° C. for some strains.

Results

Partially Purified E. coli Extract Facilitates In Vitro Reconstitution of 30S Ribosomal Subunits The temperature-sensitive nature of in vitro 30S subunit reconstitution was used to identify factors that can potentiate 30S subunit assembly at low temperature. Reconstitutions performed at low temperature (15° C.) using 16S rRNA and either TP30 or the complete set of recombinant proteins resulted in particles that sediment near 21S. As expected, when the same reaction was heated to 42° C., 30S subunits were formed. Incubation of partially-purified E. coli extract (S100) with RI at 15° C. resulted in the appearance of particles that cosediment with 30S subunits. The conversion of RI to 30S particles occurred in an S100 dose-dependent manner. These results suggested that some component(s) of the extract was responsible for and capable of facilitating 30S subunit assembly under otherwise nonpermissive conditions.

E. coli DnaK/hsp70 Chaperone System Proteins Associate with Pre-30S Subunit Intermediates Analysis of the proteins associated with the extract-treated reconstitution mixtures revealed two nonribosomal proteins cosedimenting with the assembly intermediates. Sedimentation of S100 extract alone followed by analysis of the appropriate region of the gradient revealed that one of these proteins was a contaminant that fortuitously cosediments with the intermediates. However, one protein was present only when 30S subunit intermediates (not fully formed 30S subunits) were treated with extract. This suggested that this protein specifically associated with assembly intermediates and was therefore a likely candidate for a 30S subunit assembly factor.

N-terminal protein sequence analysis (5 amino acids) of this RI-associated protein revealed a complete match to the N terminus of DnaK, a 70 kDa E. coli heat shock protein (hsp70). DnaK is a molecular chaperone that generally acts to influence protein folding (for reviews, see Bukau and Horwich, 1998; Agashe and Hartl, 2000). Western blot analysis using an anti-DnaK antibody verified that the intermediate-associated protein was DnaK, and that DnaK could associate with the intermediate either in the presence or absence of tertiary binding proteins. No DnaK was found associated with particles in the absence of extract treatment. These results indicated that DnaK can associate with pre-30S subunit intermediates in the context of a relatively crude cellular extract. This, taken together with the activation of 30S subunit assembly by extract treatment, suggested that DnaK could be an extract component involved in facilitating 30S subunit assembly.

Given the association of DnaK with the 30S subunit assembly intermediates, it was determined whether the DnaK cochaperones GrpE and DnaJ (together with DnaK:DnaK/hsp70 chaperone-system) were also associated with these particles. GrpE is a nucleotide exchange factor for DnaK that replaces bound ADP for ATP while likely altering the conformation of DnaK (Liberek et al., 1991; Dekker and Pfanner, 1997). Western blot analysis revealed that GrpE associated with pre-30S subunit intermediates that had been treated with extract. No GrpE was detected in the absence of extract pretreatment. Thus, out of the extract, both DnaK and GrpE can stably associate with pre-30S subunit assembly particles. DnaJ (40 kDa), which normally acts to stimulate substrate binding and the ATPase activity of DnaK (Wall et al., 1994), was not found associated with extract treated pre-30S particles, although it was readily detected in the extract using an anti-DnaJ antibody. Nevertheless, DnaJ might participate in 30S subunit assembly via a transient interaction, consistent with its proposed action in protein folding (for review, see Fink, 1999).

Purified DnaK/hsp70 Chaperone System Components Can Facilitate 30S Subunit Reconstitution at Low Temperature To determine if the DnaK/hsp70 chaperone system participated in 30S subunit assembly, in vitro reconstitution experiments were performed using purified DnaK, GrpE, and DnaJ. At low temperature, where in vitro reconstitution of 30S subunits is stalled, DnaK, GrpE, DnaJ, and ATP activated the conversion of RI to 30S particles. Use of a slowly hydrolyzable ATP analog (ATP-γ-S) in place of ATP inhibited conversion of RI to 30S particles. The requirement for DnaJ and ATP hydrolysis was consistent with the known role of DnaJ in accelerating the rates of ATP hydrolysis and substrate binding by DnaK (Liberek et al., 1991; Wall et al., 1994). These results indicated that DnaK, DnaJ, and GrpE, in concert with ATP hydrolysis, facilitate 30S subunit assembly under otherwise nonpermissive conditions. While the 25 unique constituents used in these studies were each individually purified to near homogeneity (>90% pure) (see Culver and Noller, 2000, and Materials and Method), the formal possibility remains that a minor contaminant also contributes to the activity. Such a component could possibly interact with a chaperone or small subunit protein and therefore by definition would be part of the 30S subunit assembly system.

Chaperone-Assembled 30S Subunits Are Authentic

To confirm that the chaperone-assembled particles were indeed 30S subunits, the association of the tertiary binding proteins, which only occurs after the RI to RI* transition, was monitored. Since S2 and S3 are tertiary binding proteins and are two of the largest small subunit proteins, their association with the different RNPs by SDS-PAGE was monitored. As expected, S2 and S3 were associated with 30S particles formed by heat activation as well as with those formed at low temperature in the presence of DnaK, DnaJ, GrpE, and ATP. The primary binding protein S4 and a collection of smaller, less well-resolved 30S subunit proteins were present in ΔRI* and in the chaperone and heat-activated 30S subunits. Since RI is relatively unstable (Held and Nomura, 1973), no proteins were detected from this purified particle, suggesting the particles were dissociating during recovery. These results indicated that the DnaK chaperone system assembled particles are authentic 30S subunits with the tertiary binding proteins associated.

The functional state of the 30S subunits produced using the DnaK chaperone system was assessed using transfer RNA (tRNA) binding (see Nomura et al., 1969; Culver and Noller, 2000), a standard assay for monitoring the functional capacity of reconstituted 30S subunits. DnaK chaperone system assembled 30S subunits bound tRNA approximately 70% as well as Δ30S subunits (Table V). A very low level of tRNA binding was observed for purified RI and ΔRI* particles (Table V). This low level of binding is likely nonspecific as it is similar to that observed in template-independent reactions. The observed difference in the tRNA binding capacity of Δ30S subunits and chaperone-formed 30S subunits is likely not reflective of any significant functional discrepancy, but perhaps purity or stability of the different particles. An additional functional test, subunit association, further supports the authenticity of the chaperone-assembled 30S subunits by demonstrating their competence in forming 70S ribosomes with natural 50S subunits. Thus, DnaK, DnaJ, GrpE, and ATP, the four components of the DnaK chaperone system, appeared to facilitate assembly of functional 30S subunits.

TABLE V

Transfer RNA Binding of Reconstituted 30S Particles

| Particle | % Binding |
|---|---|
| Δ30S | 100 ± 4 |
| RI (all) + K/J/E | 68 ± 7 |
| RI (all) | 4 ± 5 |
| ΔRI* | 3 ± 2 |

Filter binding of tRNA was performed as previously described for recombinant reconstituted ribosomal particles (Culver and Noller, 1999, 2000). RI, reconstitution intermediate; RI*, activated reconstitution intermediate.

DnaK Interacts Specifically with a Subset of Small Subunit Ribosomal Proteins

To begin to unravel the process by which the DnaK/hsp70 chaperone system acts in 30S subunit assembly, the interaction between DnaK and 30S subunit components was investigated. To this end, a complete mixture of individually purified recombinant small subunit ribosomal proteins was assayed for their ability to bind a DnaK affinity column. During the initial washes to remove non- or weakly interacting proteins, some of the DnaK appears to be liberated from the column matrix. However, a significant amount of DnaK was recovered from the column matrix after a complete round of affinity chromatography (including washes with up to 1 M KCl), suggesting that the initial loss was not significant. The identity of the DnaK binding proteins was determined by comigration with purified ribosomal proteins on SDS-PAGE in combination with mass spectrometry analysis. There was an obvious hierarchy of binding with some of the small subunit proteins appearing to not interact with DnaK, while others were capable of strongly interacting. This hierarchical binding was clearly illustrated in the elution patterns of S3 and S4. S3 began to elute early in the gradient, while S4 did not elute from the column until later in the gradient and S4 appeared to be one of the last proteins to elute from the DnaK column under the tested conditions. These interactions could play a role in in vitro 30S subunit assembly, as a concentration of 330 mM KCl is optimal for this process (Traub and Nomura, 1968; Mizushima and Nomura, 1970; Held et al., 1974).

Interestingly, in addition to the clear divisions based on strength of interaction, the DnaK binding proteins were divided into three classes based on known properties of the ribosomal proteins. The first class was comprised of those proteins that are stably associated with RI (S4, S8, S16, and S17). Of these, S4, S8, and S17 are primary binding proteins and thus play a significant role in assembly. The second class was found substoichiometrically associated with RI (S5, S12, and S19) but found fully associated with ΔRI* (Held et al., 1974), suggesting that the binding of these proteins is altered during the RI to RI* transition. Lastly, the third class binds only after RI* is formed, i.e., is composed of tertiary binding proteins (S3 and S21). The interaction of S3 and S21 with DnaK was striking, as both proteins have been implicated in small subunit function, such as tRNA binding (Ramakrishnan et al., 1986; Vladimirov et al., 1985; Graifer et al., 1989). These results suggest that DnaK may play a role both pre- and postactivation of the 30S subunit assembly intermediate. Thus, the DnaK chaperone system may act to direct formation of functional sites within the 30S subunit and perhaps play a role in the timing of functional 30S subunit production.

Since DnaK likely binds a variety of proteins while performing its role as a chaperone in vivo, the specificity of the interactions between the small subunit proteins and DnaK was assessed by using E. coli whole-cell lysate in the DnaK affinity chromatography. A subset of proteins from the cellular lysate stably interacted with DnaK. Interestingly, the same small subunit ribosomal proteins that were able to bind the DnaK column from a purified system were also found in the subset of cellular proteins associated with DnaK. Thus, these small subunit ribosomal proteins were able to interact with DnaK in the context of the whole-cell protein milieu and likely represent in vivo targets for DnaK.

DnaK can be Linked to Ribosome Biogenesis In Vivo

Given data functionally linking DnaK and small subunit components in vitro, the possibility of an in vivo interaction was investigated. Previously, it had been shown that ribosome biogenesis was altered in a particular allele of dnaK (dnaK756) (Georgopoulos et al., 1973; Yochem et al., 1978) under nonpermissive conditions (high temperature and low salt) (Alix et al., 1993). To address whether the interactions observed between DnaK and the small subunit ribosomal proteins in vitro could occur in vivo, suppression of the temperature-sensitive phenotype of dnaK756 by overexpression of some of the small subunit ribosomal proteins was assayed. Three primary binding proteins, S4, S8, and S15, were chosen as a test set. Each of these proteins plays a critical role in 30S subunit assembly, and moreover, each differentially interacts with DnaK as demonstrated in the affinity chromatography experiments.

No significant interaction between S15 and DnaK was observed, S8 demonstrated an intermediate level of binding, and S4 appeared to be one of the strongest DnaK binders. To test for suppression, the genes for these proteins were cloned into a vector that allows inducible overexpression in the dnaK756 background. Suppression of the temperature-sensitive (ts) growth phenotype was assayed by dilution plating and then trends confirmed by measuring doubling times. Overexpression of S4 clearly rescued the ts phenotype of dnaK756, although the growth rate did not return to that observed under permissive conditions. Nevertheless, the increase in growth in the presence of S4 at high temperature was very striking, particularly since the strain containing S4 grew less well than the strain harboring the empty vector at permissive temperature. Overexpression of S15 appears to have had no effect on the growth of dnaK756, while overexpression of S8 afforded a slight rescue of dnaK756 at high temperature. These results were intriguing since it appeared there was a correlation between the interactions observed by affinity chromatography and the suppression of the ts dnaK756 phenotype.

Next, it was determined if overexpression of S4 could alter the effect of dnaK756 on ribosome biogenesis. Due to the very slow growth of dnaK756 at high temperature in low-salt media, initially the cultures were grown in rich media (under these conditions dnaK756 is not temperature sensitive, although for consistency, the two temperatures are referred to permissive and nonpermissive) to allow analysis of polysomes from an equivalent number of cells. At the permissive temperature, polysome profiles from both strains looked similar and like those from wild-type strains. However, at the nonpermissive temperature, the polysome profiles were dramatically different. When dnaK756 containing the empty vector was grown at high temperature, there was a significant decrease in the number of 70S ribosomes, and polysomes were not detected. In contrast, when dnaK756 harboring the vector containing S4 was grown at the nonpermissive temperature, the polysome profile more closely resembled those from the permissive temperature. The rescue did not appear to be complete, again correlating with the doubling time of the strains. Since these strains were grown under conditions where dnaK756 is not temperature sensitive, it is possible that the full effect of this mutation is not manifested. In an attempt to address this possibility, the strains were grown under conditions where the temperature-sensitive phenotype was apparent. Although far fewer cells could be harvested from the dnaK756/vector strain at the nonpermissive temperature, analysis of ribosomes revealed a marked change in the distribution of subunits to 70S ribosomes. Thus, it appears that not only is the number of ribosomes altered in this strain but the relative distribution of subunits to ribosomes is also altered. Coordinated synthesis of components for both subunits may account for the observed decrease in both small and large subunits. Characterization of the particles produced under these conditions has proven refractory due to the small amount of material that was obtained. Overexpression of S4 resulted in more wild-type-like profiles, although complete rescue was not observed. These results suggested that DnaK can functionally interact with ribosomal components in vivo and that this interaction has an effect on ribosome assembly.

Discussion

Figure 2:
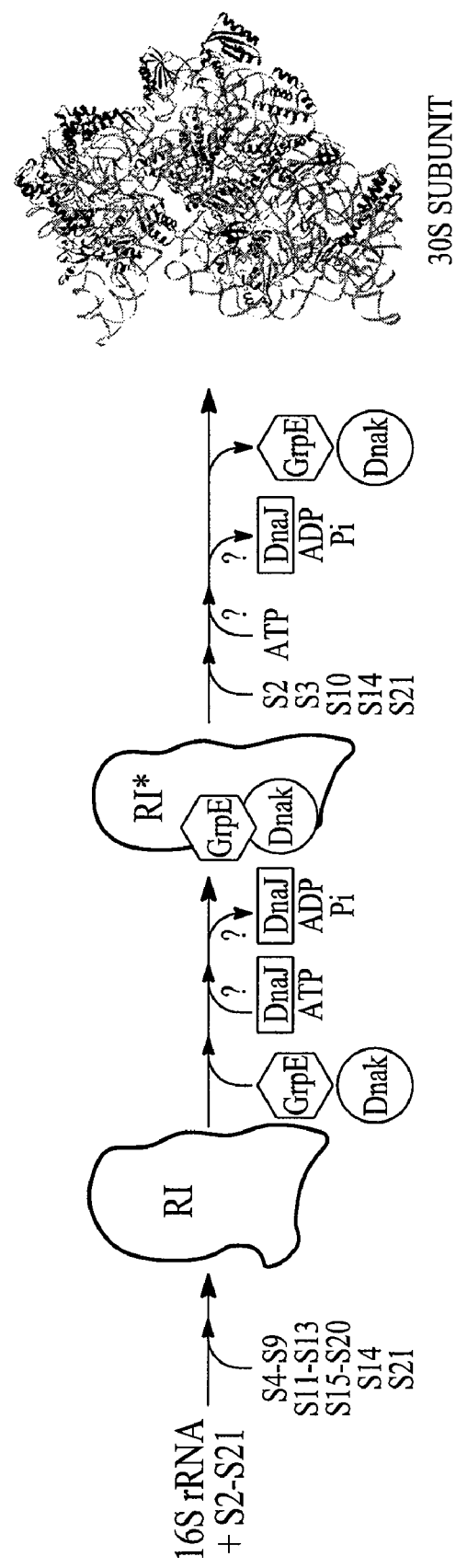
FIG. 2. Putative model for 30S subunit assembly. RI, reconstitution intermediate; RI*, activated reconstitution intermediate.

Thus, the DnaK/hsp70 chaperone system can facilitate 30S subunit assembly. Components of the DnaK chaperone system (DnaK and GrpE) were shown to stably bind pre-30S particles (FIG. 2). Hydrolysis of ATP in combination with the action of DnaK, DnaJ, and GrpE were all involved in facilitating 30S subunit assembly. Evidence also suggested in vitro and in vivo interactions between DnaK and 30S subunit components. Ribosome biogenesis was also altered by these in vivo interactions. These results have led to a model for 30S subunit assembly (FIG. 2). This model reflects data presented here and the likelihood that the chaperone components function in 30S subunit assembly in a manner similar to their proposed functions in protein folding (Burston and Clarke, 1995).

Generally, DnaK is assisted in substrate binding by DnaJ (Schmid et al., 1994). Therefore, by analogy (FIG. 2), DnaK binds to the substrate ribonucleoprotein (RNP), in a reaction potentially augmented by DnaJ and ATP (or ATP hydrolysis). GrpE, which can be found associated with the intermediate, is likely tethered to the complex by its well-documented interaction with DnaK (Schonfeld et al., 1995; Wu et al., 1996). When DnaK is in an ADP-bound state, it likely remains bound to the RNP. It is possible that DnaK binding is responsible for the RI to RI* transition and that continued association of DnaK with the RNP could block further assembly. If the role of GrpE in 30S subunit assembly is similar to that in protein folding, it is likely involved in exchange of ADP/Pi for ATP on DnaK and that this exchange results in conformational changes within DnaK which occur concomitantly with release of RI* from the chaperones. These changes could result in the transition of RI to RI*(if DnaK binding is not sufficient for this transition) and may include an initial interaction with the tertiary binding proteins. Once released from DnaK, the rearranged, competent intermediate could undergo the final stages of assembly to form a functional 30S subunit.

The interaction of the substrate RNP with DnaK may occur directly via DnaK binding to one or more of the small subunit proteins, or DnaK may have affinity for 16S rRNA as well. An interaction between DnaK and 16S rRNA would not be completely unprecedented; it has been shown that chaperones belonging to both the hsp60 and hsp70 systems can interact with RNA (Ruggero et al., 1998; Okada et al., 2000; Zimmer et al., 2001). Recent work has also shown that the binding of DnaK to RNA is affected by the presence of its cochaperones GrpE and DnaJ (Zimmer et al., 2001). Therefore, the interaction between the DnaK chaperone system and the 30S subunit assembly intermediate RNP may be mediated by 16S RNA. Alternatively, DnaK may bind directly to some of the small subunit ribosomal proteins. The proteins that were identified as DnaK binding proteins are good candidates for mediating these interactions. In addition, some of the unique structural features of the small subunit ribosomal proteins (Brodersen et al., 2001) could also prove important for DnaK chaperone system binding to the 30S subunit assembly intermediate RNP. These interactions might occur in a manner analogous to those documented for protein substrate binding (for reviews, see Bukau and Horwich, 1998; Fink, 1999). Hence, RNA or protein binding may mediate the association of DnaK with the pre-30S particles. Moreover, a combination of these binding events may play a role, as they are not mutually exclusive. Also, it is possible that features unique to this RNP are involved in binding. Regardless of the specifics, it appears that components of the DnaK chaperone system act in concert in RNA, RNP, and protein binding/folding and that the mechanisms involved in the interaction with/folding of these different substrates may share similar characteristics.

A role for DnaK/hsp70s in ribosome assembly has previously been suggested. Growth of a temperature-sensitive mutant dnaK strain (dnaK756) at the nonpermissive temperature resulted in a defect in ribosome biogenesis (Alix et al., 1993). However, defects in other cellular processes were also observed in this dnaK strain, and thus the specificity of the alteration on ribosome assembly has not been easy to address. Overexpression of small subunit proteins that bind DnaK can partially suppress the temperature-sensitive phenotype and partially rescue the ribosome assembly defect of this dnaK allele. The known roles and structures of these proteins may offer insight into how DnaK influences 30S subunit assembly. A role of hsp70s in ribosome biogenesis may not be limited to E. coli. Two hsp70 homologs, Ssa1p and Ssb1p, have been found associated with ribosome assembly intermediates in yeast (Harnpicharnchai et al., 2001). Thus, it appears that the participation of hsp70 chaperone systems in ribosome biogenesis may be a highly conserved phenomenon.

Thus, the DnaK/hsp70 chaperone system has a role in 30S ribosomal subunit assembly in vitro. Moreover, that DnaK and small subunit components functionally interact in vivo. In addition to revealing the possible existence of ribosome assembly factors, these findings link two very highly conserved systems, ribosomes and hsp70s, thus raising the possibility that hsp70 chaperone systems act during ribosome assembly throughout phylogeny. However, given that DnaK is not essential (Paek and Walker, 1987) and the cellular importance of an active pool of ribosomes, there may be other yet to be identified factors involved in ribosome biogenesis.

EXAMPLE III

Comparison of Two 30S Ribosomal Subunit Preparations

Alix et al. (2003) used two main approaches to test whether the DnaK chaperone system (see Example II) facilitates functional 30S subunit assembly. In the first approach, they assessed the kinetics of in vitro 30S subunit reconstitution at various temperatures in the presence and absence of the DnaK chaperone system. At different time points during the reconstitution, they assayed the ability of these particles to participate in poly(U)-directed polyphenylalanine synthesis. They found the same levels of polyphenylalanine synthesis in the presence and absence of purified chaperone components at each given temperature. In the second approach, ribosomal components from an E. coli dnaK null strain (BB1553; grown at the permissive temperature) were compared to wild-type subunits. Ribosomal subunits, both 30S and 50S, reconstituted with components isolated from the dnaK knockout strain were shown to function in their polyphenylalanine synthesis assay (Alix et al., 2003). Also, 2D-PAGE of ribosomal proteins isolated from particles from the dnaK null strain grown under permissive conditions were shown to be similar to proteins isolated from a wild-type strain (Alix et al., 2003). Additionally, ribosomal subunits from both the dnaK knockout and wild-type strains were stable when incubated up to 50° C. in a 1 mM $MgCl_2$, 200 mM $NH_4Cl$ buffer (Alix et al., 2003). From these studies, Alix et al. (2003) concluded that the DnaK chaperone family was not sufficient to facilitate reconstitution of 30S subunits.

Figure 3:
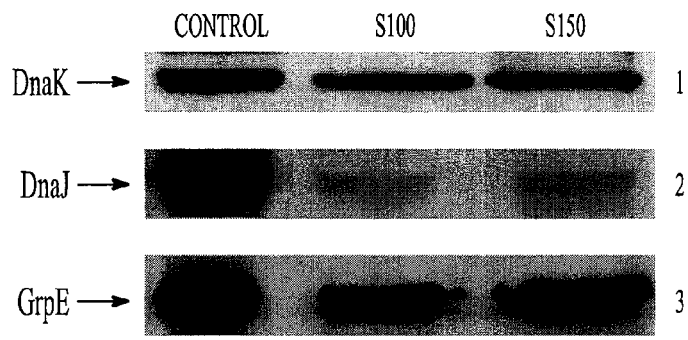
FIG. 3. Western blot analysis of E. coli extracts for the DnaK chaperone system. Control, 0.5 µg of purified protein (DnaK, DnaJ or GrpE) (from StressGen Biotech). S100, 20 µg S100 extract; S150, 20 µg S150 extract. Lane 1, membrane probed with monoclonal anti-DnaK antibody. Lane 2, membrane probed with polyclonal anti-DnaJ antibody. Lane 3, membrane probed with anti-GrpE antibody. All antibodies were purchased from StressGen Biotech. S100 prepared as reported in Maki et al. (2002). S150 prepared as reported by Nierhaus (1990).

There are three major issues that bear on the interpretation of the data of Alix et al. (2003). The first is a problem inherent in their polyphenylalanine synthesis assay. To perform the assay, the authors added an E. coli crude high-speed supernatant fraction, S150 (Alix et al., 2003). All of the DnaK chaperone components are present in an S100 extract (Example II). To determine whether those components are also present in a S150 extract, a S150 extract was prepared as described by Alix et al. (2003) and Nierhaus (1990). Western blot analysis of the S150 extract revealed that DnaK, DnaJ and GrpE were all present at levels comparable to those found in S100 extract (FIG. 3). Thus, while Alix et al. (1993) went to some lengths to determine that the 30S subunits used to prepare the components for these experiments were devoid of DnaK, they appeared to have overlooked another source of chaperone contamination. Therefore, their reconstitutions were never actually performed in the absence of the DnaK chaperone system.

A second major problem is that Alix et al. (1993) assayed crude reconstitution mixtures for polyphenylalanine synthesis capability. In marked contrast, as described in Example II and Maki et al. (2002), tRNA binding assays were performed on sucrose gradient purified particles, which were washed and concentrated on molecular sieving filters with a molecular weight cut-off of 100,000. Here, it appears that assaying a purified population is important for monitoring differences, as problems detecting activity were found using a crude reconstitution mixture (data not shown). The ability to monitor changes in many reactions has been shown to be dependent on use of a minimal, purified in vitro system, see, for example, Samaha et al. (1995), and so is not unique to the ribosomal system. The use of purified particles is also relevant to the question raised by Alix et al. (1993) of possible assembly during the tRNA binding assay. Since sucrose gradient sedimentation and further purification as described herein were used to isolate particles for tRNA binding, only proteins that were stably associated with the 16S rRNA-containing particle were present in the tRNA binding assay. This precludes the binding of additional non-associated proteins during the tRNA binding assay at 37° C. Thus, incubation at 37° C. alone could not account for the results in Example II and Maki et al. (2002). Related to these issues is the manner in which polyphenylalanine synthesis activity measured by Alix et al. was reported (Alix et al., 2003). The activity is given as phe per ribosome vs. time of reconstitution; yet since aliquots of the crude 30S subunit reconstitutions were removed and directly used in the polyphenylalanine assay, it is unclear how the amount of ribosome per reaction was determined. Purification of the reconstituted particles may not only be critical to detect activity, but it also allows-functional capacity to be more accurately measured.

A third issue is one of reaction conditions. Alix et al. (2003) used incubation at 20° C. for their most restrictive reconstitution conditions and subjected their particles to an additional incubation at 20° C. for 2 hours during the polyphenylalanine synthesis assay. In contrast, 15° C. was employed as the standard restrictive reconstitution temperature in Example II. These differences may explain the differences in the observed results, since at 20° C., a sub-population of particles was able to form 30S particles in the absence of any additional factors (data not shown), and the resulting higher background decreases the sensitivity of the assay. Thus, the conditions used by Alix et al. (2003) decrease the dynamic range within which changes in assembly can be monitored.

Figure 4:
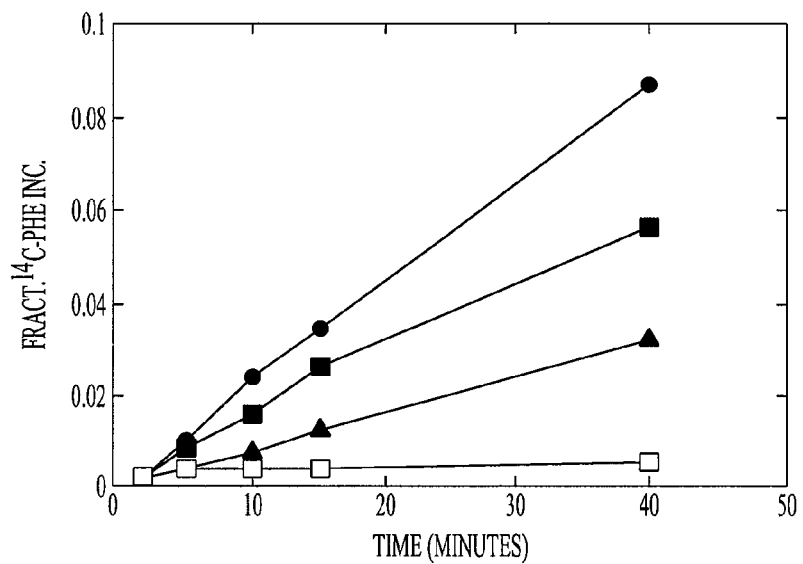
FIG. 4. Polyphenylalanine synthesis by purified in vitro reconstituted E. coli 30S particles. Reconstitutions were performed under the conditions described in Alix et al. (2003). Polyphenylalanine generated by purified 30S particles reconstituted under normal, high temperature (42° C.) conditions (●), compared to natural 50S subunits alone (□), or particles reconstituted at low temperatures (20°, 21S) (▲) or as for the 21S reconstitution but in the presence of the DnaK chaperone system (■). Chaperone conditions were similar to those of Maki et al. (2002) (16S rRNA:DnaK:DnaJ:GrpE 1:1:1:2 with 1 mM ATP). The polyphenylalanine synthesis was carried out essentially as described in Southworth et al. (2002) by incubating 30S particles and 50S subunits (0.3 µM) with polyuridine (0.35 mg/ml), $^{14}C$ Phe-tRNA$^{Phe}$, His-tagged EF-G (0.3 µM), His-tagged EF-Tu (2 µM), GTP (1.4 mM), phosphoenolpyruvate (3.5 mM) and pyruvate kinase (14 µg/ml). Reactions were carried out in 80 mM HEPES, pH 7.6, 13 mM MgCl$_2$ and 100 mM KCl.

In previous studies, tRNA binding was used as a functional assay for the reconstituted 30S subunits because it is highly sensitive to defects in structure and assembly. In contrast, Alix et al. (2003) used a polyphenylalanine synthesis assay which, in addition to the aforementioned potential contamination with assembly factors, is also dependent on the presence of natural 50S subunits which can often mask deficiencies in 30S subunit function. In the experiment shown in FIG. 4, the chaperone contamination problem is addressed with a completely defined polyphenylalanine synthesis assay that utilizes purified translation factors and pre-charged tRNAs (Southworth et al., 2002), eliminating the requirement for S100 or S150 extract, to monitor function of sucrose gradient purified reconstituted 30S subunits. These experiments show that 30S subunits assembled at low temperature in the presence of the DnaK chaperone system are more active than the 21S intermediate, but less active than 30S subunits formed by heat activation (FIG. 4). However, the overall differences are less than those observed in the tRNA binding assay. This difference may be attributable to the fact that the reconstitutions were performed at 20° C., following the protocol of Alix et al. (2003). As mentioned above, the activity attributable to RI is higher when it is formed at 20° C., resulting in an apparent lower level of stimulation by the DnaK chaperone system. The results of the polyphenylalanine synthesis assays described above are consistent with previous conclusions that the DnaK chaperone system facilitates assembly of functional 30S subunits.

The second major area discussed by Alix et al. (2003) is whether DnaK plays a role in ribosome biogenesis in vivo. Toward this end, they examined ribosomes and ribosomal components formed in a dnaK null strain. They observed that there was virtually no difference in thermostability between ribosomes isolated from dnaK knockout or wild-type strains, when the knockout is grown under the permissive conditions (Alix et al., 2003). This is not surprising, as Alix and colleagues have previously reported that " . . . . DnaK acts during ribosome assembly itself, and not by stabilizing mature ribosomes or protecting them from thermal injury (Alix et al., 1993)" (El Hage et al., 2001). Indeed, it was this same work that first reported a role for DnaK in ribosome biogenesis in vivo using the temperature sensitive strain, dnaK756, at the non-permissive temperature (Alix et al., 1993). Thus, while the thermostability of ribosomes isolated under permissive conditions from the ΔdnaK strain might be of interest, its bearing on the present findings is questionable.

The explanation for the in vivo results in Maki et al. (2002), according to Alix et al. (2003), was the partial rescue of dnaK756 phenotypes by overexpression of S4. In particular, Alix et al. (2003) suggested that suppression by S4 of the altered polysome profiles in dnaK756 was due to its role as a translational repressor. This is a possibility; however, S8, another translational repressor, was also overexpressed under the same conditions and did not see the same level of suppression observed with S4. This suggests that changes in control of ribosome component production may have some effect in these experiments, but it is unclear if this can account for the complete S4 result. Given the complications of in vivo ribosome biogenesis, all of these ideas are based on pure speculation. Therefore, while the role of the DnaK chaperone system in ribosome biogenesis in vivo is still not well understood, it remains clear that a role for these chaperones in 30S subunit assembly can be demonstrated using a purified in vitro system.

The assembly of ribosomes is a highly complicated process. Given the importance of ribosome assembly to cell physiology there are likely many factors that are involved in this process. The approach of searching for extrinsic 30S subunit assembly factors focused on a small step in this assembly process and has thus far led us to the DnaK chaperone system. As previously suggested (Maki et al., 2002), since DnaK is not essential (Paek et al., 1987) and given the importance of ribosome biogenesis to cell viability, it is likely that other factors involved in ribosome biogenesis have yet to be identified. It is highly likely that such factors facilitate ribosome assembly in the ΔdnaK strain.

EXAMPLE IV

As described above, assembly of the *E. coli* 30S ribosomal subunit can be studied in vitro utilizing natural 16S rRNA and either TP30 (Total Proteins from the 30S subunit, Traub et al., 1969) or individually purified ribosomal proteins (r-proteins) which are either natural (Mizushima et al., 1970; Held et al., 1974) or recombinant (Culver et al., 1999). While 30S subunit reconstitution can proceed in vitro, there is a sharp temperature-dependence to this reaction (Traub et al., 1969; Held et al., 1973). At low temperature a specific 16S rRNA-containing pre-30S subunit particle (RI: reconstitution intermediate; see FIG. 5) is formed and further assembly cannot continue without a shift to higher temperature.

The temperature-dependence of 30S subunit assembly has been used to develop an assay to identify extra-ribosomal assembly factors that can bypass the low temperature stall in 30S subunit assembly (Maki et al., 2002). Initial studies begin with a crude *E. coli* extract that could facilitate 30S subunit assembly under non-permissive conditions, and the DnaK chaperone system was identified as a component of the extract that played a role in 30S subunit assembly (Maki et al., 2002). This system allowed biochemical characterization of the role played by the DnaK chaperone system in 30S subunit assembly (Maki et al., 2002).

The DnaK chaperone system (or hsp70 chaperone system), composed of DnaK, DnaJ, GrpE and ATP, has been well studied for its role in protein folding (Bukau et al., 1998; Agashe et al., 2000). The DnaK chaperone system can circumvent the heat requirement of in vitro 30S subunit reconstitution (see FIG. 5 and Example II). The ribosomal particles resulting from low temperature DnaK chaperone system reconstitutions cosediment with, and have the same protein complement as, 30S subunits formed under permissive conditions (Maki et al., 2002). The 30S subunits formed via chaperone facilitation were shown to be functional in transfer RNA binding (Maki et al., 2002) and in template directed peptide bond formation, poly-U templated polyphenylalanine synthesis (Maki et al., 2003). As noted above, the functional state of DnaK chaperone system formed 30S subunits was an issue raised in Alix et al. (2003). However, as described herein, the manner in which the factor-treated 30S particles are handled prior to analysis has a dramatic effect on the monitored output. Careful procedures appear to be required to remove bound chaperone proteins following low temperature incubation from in vitro formed 30S ribosomal particles. This removal has been correlated with recovery of functional 30S subunits. A general scheme that allows isolation of functional 30S particles is outlined in FIG. 6.

Materials and Methods

All glassware must be baked at approximately 220° C. for >8 hours before use to avoid nuclease contamination. Also to minimize the likelihood of nuclease contamination, buffers are purified using Millipore Steritop 0.22 μm GP Express Plus filtration devices and Pipetman tips must be autoclaved before use. Microcentrifuge tubes are purchased from Marsh (Rochester, N.Y.) and are certified nuclease-free.

Reagents 16S rRNA used in 30S subunit reconstitution and 30S subunits used for controls and TP30 isolation can be prepared as described by Moazed et al. (1986). Total proteins isolated from 30S subunits, TP30, are prepared as described by Nierhaus (1990). Recombinant 30S ribosomal proteins are prepared as described in Culver et al. (1999 and 2000). DnaK, DnaJ, and GrpE were purchased from Stressgen Biotechnologies Corporation, Victoria, B. C. Canada. ATP was purchased from Pharmacia. Nikkol was purchased from Calbiochem. Tween-20 was purchased from Fisher Scientific.

Buffers

Buffer A or Reconstitution A buffer (RA+): 80 mM K$^+$-Hepes (pH 7.6), 20 mM MgCl$_2$, 330 mM KCl, and 0.01% Nikkol (store at 4° C.). Buffer D: 80 mM K$^+$-Hepes (pH 7.6), 20 mM MgCl$_2$, 1 M KCl, 6 mM α-mercaptoethanol (BME) (store at 4° C.). Buffer F: 20 mM K$^+$-Hepes (pH 7.6), 20 mM MgCl$_2$ (store at 4° C.). Buffer H: 80 mM K$^+$-Hepes (pH 7.6), 20 mM MgCl$_2$, and 0.01% Nikkol (store at 4° C.). Sucrose gradient buffer: 1×=50 mM Tris-HCl (pH 7.6 at 4° C.), 20 mM MgCl$_2$, 100 mM KCl; 5×=250 mM Tris-HCl (pH 7.6 at 4° C.), 100 mM MgCl$_2$, 500 mM KCl (store at 4° C.).

Results

Details for the in vitro reconstitution of functional 30S ribosomal subunits in the absence of exogenous factors have been previously described (Culver et al., 1999; Traub et al., 1981) but are highlighted here for continuity, and aspects of chaperone-facilitated 30S ribosomal subunit reconstitution are detailed as needed for clarity. For each batch of 16S rRNA, TP30 and recombinant proteins, the appropriate ratios of components for 30S subunit formation must be empirically determined. Generally for TP30, a 1 to 5 fold molar excess over 16S rRNA is used and for the recombinant proteins, a 4 to 9 fold molar excess over 16S rRNA is used. An excess of ribosomal protein (r-protein) mixture may be required due to inactivation of some of the proteins during the extensive isolation procedure (Nomura et al., 1969; Culver et al., 1999). Also, for the recombinant r-proteins it is possible that they are not appropriately post-translationally modified and therefore a greater excess might be required for function (Culver et al., 1996). Thus, for each new preparation, titration of protein versus RNA amounts are performed to ensure that 30S subunit reconstitution conditions are optimal. These reconstitutions are performed at 42° C. and at 0.4 μM 16S rRNA (final concentration; see below). In chaperone-assisted reconstitutions, 16S rRNA is used in a 1:1 ratio with DnaK and its cochaperone DnaJ, and in a 1:2 ratio with DnaK's other cochaperone, GrpE. ATP in the reconstitution at a concentration of 1 mM has proven to be the most effective with the DnaK chaperone system (Maki et al., 2003; unpublished results). Also, 15° C. appears to be optional for stalling 30S subunit assembly in vitro at the Reconstitution Intermediate, RI (FIG. 5); at 20° C. formation of some functional particles can be observed (Maki-et al., 2000) suggesting that assembly can proceed slowly and therefore it is more difficult to observe differences between chaperone-treated and untreated reconstitutions (Maki et al., 2003; unpublished results).

DnaK Chaperone System Facilitated 30S Subunit Reconstitution

Figure 5A:
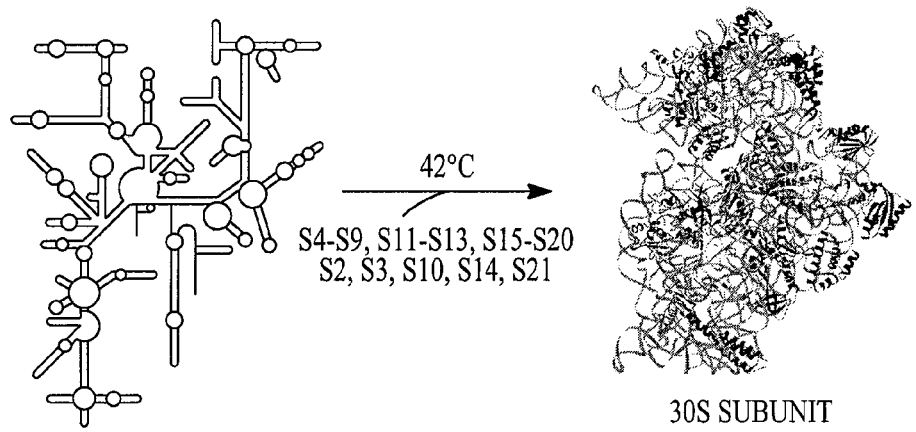
FIG. 5. Stepwise in vitro reconstitution of E. coli 30S ribosomal subunits. The secondary structure of 16S rRNA is shown in gray. The ribosomal proteins that assemble early are shown in red and those that assemble later are shown in blue. The 30S subunit structure was prepared using Ribbons. A). Schematic of standard 42° C. in vitro reconstitution of 30S subunits. B). Schematic of standard stepwise in vitro reconstitution of 30S subunits. At low temperature, a subset of ribosomal proteins (in red) bind to 16S rRNA and form the Reconstitution Intermediate (RI). Heat treatment at 42° C. allows RI to undergo a conformational change to form the activated Reconstitution Intermediate (RI*) and then the remaining ribosomal proteins (in blue) can bind at low or high temperature to form 30S subunits. C). Schematic of DnaK chaperone-facilitated 30S subunit in vitro reconstitution. RI is formed as described in panel A, but addition of DnaK, DnaJ, GrpE and ATP circumvents the necessity of heat treatment and assembly of 30S subunits can proceed at low temperature.
Figure 5B:
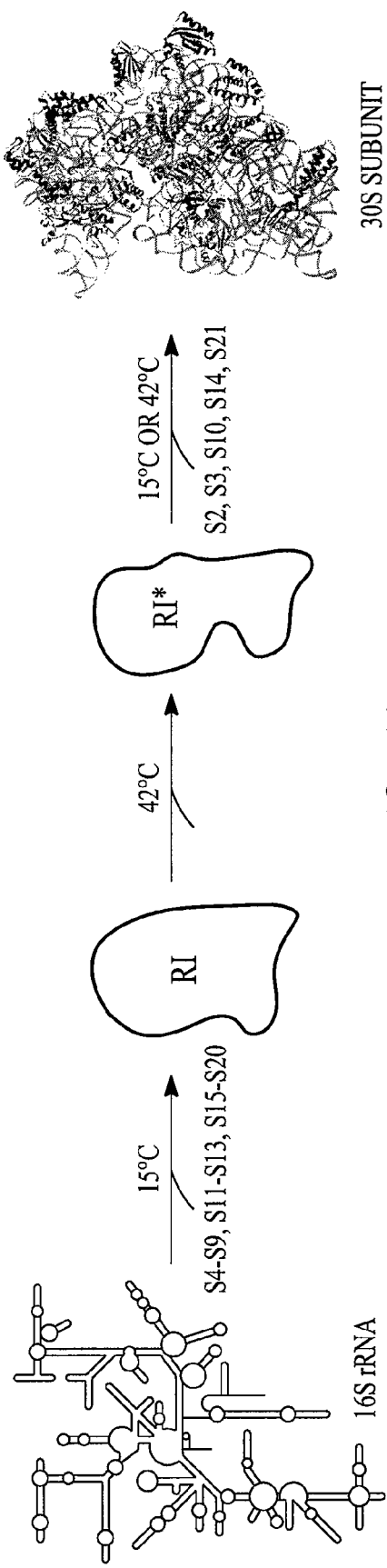
Figure 5C:
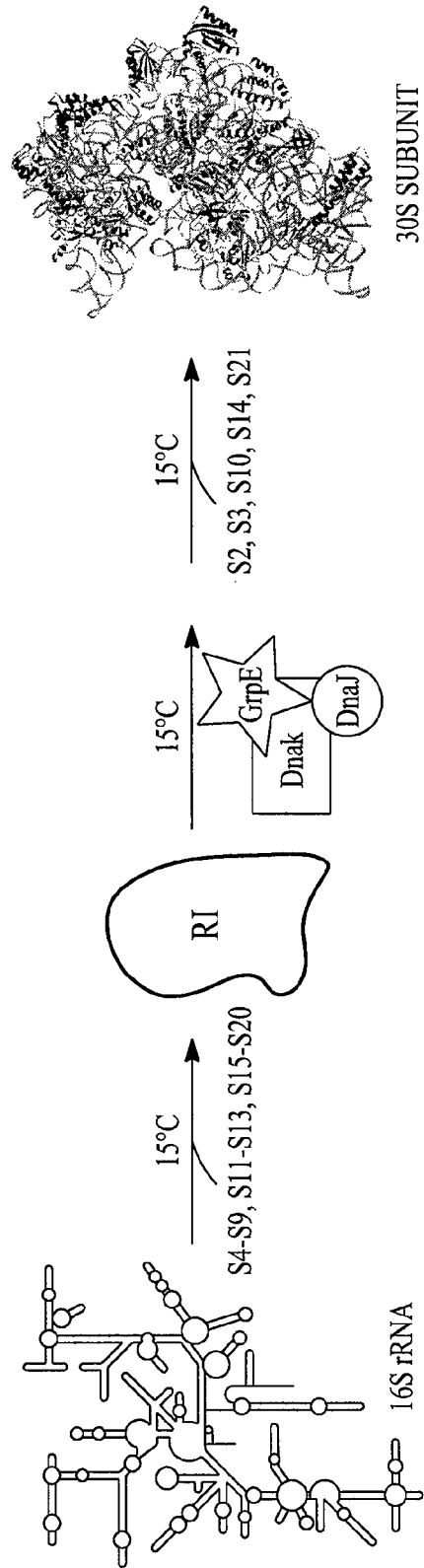

Generally, 30S subunit reconstitutions are performed as described in Culver et al. (2000) and Traub et al. (1981). In a standard reconstitution, 40 pmol of 16S rRNA was used, and this is referred to as a 40 pmol reconstitution and the final concentration of 16S rRNA would be 0.4 μM (100 μl reaction volume final). Since r-protein mixtures were stored in 1 M KCl (Buffer D) and reconstitution proceeds at 330 mM KCl (Buffer RA+), the KCl concentration must be readjusted after addition of any protein mixture during the reconstitution reaction. In a standard reconstitution, 40 pmol 16S rRNA (in Buffer F) was mixed with equal volume of Buffer H by pipetting up and down, followed by brief centrifugation and incubation at 42° C. for 20 minutes. For standard reconstitutions, samples can be kept briefly at room temperature during subsequent additions of components; however, for low temperature factor-dependent reconstitutions, after heat activation of naked 16S rRNA at 42° C. for 20 minutes, the RNA was then cooled on ice for 15 minutes (FIG. 6) prior to addition of the r-proteins, and samples were maintained at 15° C. during addition of subsequent components. This was required since the reconstitution proceeds at 15° C. (see above and FIG. 6) instead of 42° C. All samples were mixed by pipetting up and down followed by centrifugation at top speed for 5 seconds prior to incubation at 42° C. (standard reconstitution) or 15° C. (low temperature reconstitution). To this reaction, the r-proteins were added and the buffer was adjusted such that optimal ionic concentration (330 mM KCl; Buffer RA+) and final concentration of 16S rRNA (0.4 μM) were obtained. For standard reconstitutions, the reactions were incubated at 42° C. for 40 to 60 minutes; for low temperature reconstitutions, the reactions were incubated at 15° C. for 40 minutes. This results in 30S subunit formation (42° C.) and RI formation (15° C.) (FIG. 5).

For chaperone-facilitated reconstitution, after addition of all the r-proteins and incubation at 15° C., for the standard 0.4 μM 16S rRNA reconstitution in 100 μL total volume, 40 pmol DnaK and DnaJ were added along with 80 pmol GrpE and 100 nmol ATP. Generally, the stocks of DnaK, DnaJ, and GrpE that are obtained from Stressgen are highly concentrated and thus the ionic concentration of the reconstitutions is not significantly altered by their addition. The chaperone system components were generally added in this order and each addition was mixed by tapping the side of the microcentrifuge tube. After the addition of ATP, the reaction mixtures were pipetted up and down and then briefly centrifuged at top speed for 5 seconds. The reconstitutions were then allowed to incubate at 15° C. for 2 additional hours. Following the 15° C. incubation, the reactions were put on ice prior to loading on sucrose gradients. For reactions with no addition of chaperones, the standard reconstitution was maintained at 42° C. while the low temperature reaction was maintained at 15° C. These reactions act as controls (30S subunit formation from the 42° C. samples and stalled Reconstitution Intermediate for the 15° C. samples) to monitor the effectiveness of the chaperone-facilitated reconstitution. Also, for a standard stepwise reconstitution, particles that were initially incubated at 15° C. should be shifted to 42° C. to demonstrate the progression from RI to 30S subunits.

Purification of in vitro Assembled 30S Ribosomal Subunits

Once in vitro reconstitution of particles was complete, the particles were loaded on 10 to 40% sucrose gradients in 1× sucrose gradient buffer. Sucrose gradients were prepared using a modification of a procedure in Culver et al. (2000). A 60% sucrose solution was prepared weight to volume in H$_2$O, Six 14×89 mm ultraclear ultracentrifuge tubes (Beckman) were marked to designate the high fill line using the SW41Ti marker block provided with the Biocomp Gradient Master (model 106). For six (11 mL) sucrose gradients, 50 mL of a 10% and a 40% solution in 1× sucrose gradient buffer were made. A 10% sucrose solution in 1× sucrose gradient buffer was prepared by mixing 8.3 mL 60% sucrose with 10 mL 5× sucrose gradient buffer and 31.7 mL H$_2$O. 33.3 mL 60% sucrose was mixed with 10 mL 5× sucrose gradient buffer and 6.7 mL H$_2$O to prepare a 40% sucrose solution in 1× sucrose gradient buffer. An 11 mL 10% to 40% sucrose gradient in 1× sucrose gradient buffer was prepared by first adding the 10% solution to a 14×89 mm ultraclear ultracentrifuge tube to the high fill line mark using a 10 mL sterile plastic pipette. The 40% solution was then added slowly to the bottom of the tube using a canula (provided with the Biocomp gradient master) attached to a 20 mL syringe. This "displaces" the 10% solution from the bottom of the tube. Care should be taken to not allow drops of sucrose to adhere to the side of the tube and to minimize mixing as the 40% sucrose solution is added. Tubes were then capped with parafilm (or the high fill caps provided with the Biocomp gradient master) and placed on the gradient master. The gradient master is set for Time=1:48, Angle=81.5 and Speed=17 (as specified in the Biocomp Gradient Master Operator's manual) and this operation is run. Once this cycle has been completed, gradients were stored upright at 4° C. for 2 to 12 hours prior to ultracentrifugation. Prior to loading samples onto the gradient, 250 μL in excess over the sample volume must be carefully removed from the very top of the gradient using a P1000 Pipetman. For example, for a 100 μL (40 pmol) reconstitution, 350 μL is removed and then the 100 μL sample is carefully layered on top using a P200 Pipetman. Sucrose gradients are then balanced to within 0.1 grams using an analytic balance and addition of the 10% sucrose solution in 1× sucrose gradient buffer via careful application using a Pasteur pipette. The samples are then centrifuged in an SW41Ti rotor (Beckman) in a Beckman Ultracentrifuge for 15.5 hours at 32,000 r.p.m at a temperature of 4° C. Sucrose gradients are analyzed using a density gradient fractionator (Brandel/Isco model 183) with detection filters set to observe absorption at 254 nm, where RNA absorption is maximal. This system results in the top of the gradient being resolved first, i.e., it pumps from the bottom. Distinct samples were collected from the eluted gradients by hand into eppendorf tubes after they have passed through the in-line UV detector. The samples were retained on ice until all gradients were analyzed and appropriate fractions collected. Once all samples were collected, absorbance at 254 nm of each purified sample is taken in a spectrophotometer using a 1 mL quartz cuvette. This allows equal amounts (in terms of RNA content) of each sample to be further analyzed. In this manner, either all RNA containing peaks can be collected and analyzed or only species that sediment at certain positions can be compared. Also, for some applications (such as initial screening or determination of which ribosomal proteins are associated with the particle) it may not be essential that equal amounts of particles are evaluated.

For most applications, the samples are concentrated and sucrose is removed prior to further analysis. Ultraconcentrators have proven to be very useful for these purposes and this treatment is likely gentler than precipitation methods. Centricon ultraconcentrator 100s (molecular sieving filters with a molecular weight cutoff of 100 kDa; Amicon) were treated before use by application of 150 μL 10% Tween-20 to the surface of the filter. The Tween-20 was added using a P200 Pipetman and care is taken to avoid contact between the pipette tip and the filter. The Tween solution was allowed to sit on the membrane for five minutes and was then rinsed thoroughly with copious amounts (at least 10 mL) of distilled $H_2O$ using a squirt bottle. Once the membrane was wetted, it was never allowed to dry out. After rinsing with $H_2O$, each membrane was rinsed with 500 μL of 10% sucrose in 1× gradient buffer to equilibrate it before the sample was introduced. Finally, this buffer was discarded and the samples were loaded onto the washed Centricons. The total volume of each sample is raised to 2 mL with RA+ buffer. The Centricons are then placed into a JA-20 rotor (Beckman; with rubber adaptors, Corning Corex) and spun in the high speed centrifuge at 2,000 r.p.m. Once the samples were concentrated to a small volume (100 to 200 μL after 30 to 45 minutes), the Centricons were filled with RA+ buffer once again. This was done twice, so the original particles were washed with 6 mL of RA+ buffer and concentrated to a final usable volume (about 100 μL). Centricons were then retro-spun by placing the retentate vial on the sample chamber, inverting the sample chamber and then centrifuging for one minute at 2,000 r.p.m. in a JA-20 rotor with adaptors to collect the samples. Retentate vials were placed on ice, a P200 or P 1000 Pipettman was used to determine the volume of recovered sample and then the volumes are equalized with cold RA+ buffer.

Figure 6:
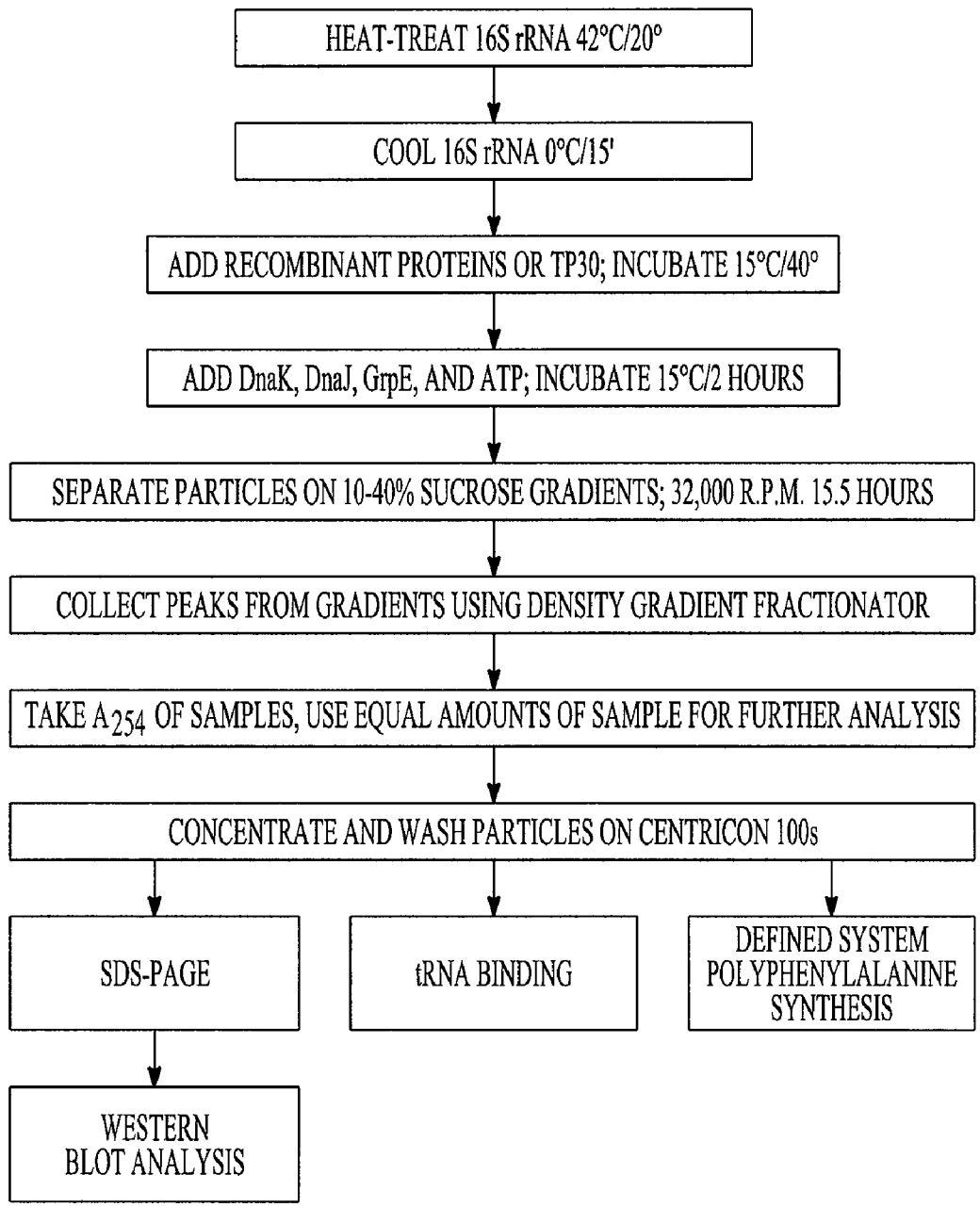
FIG. 6. Factor-facilitated in vitro ribosome assembly: Analysis flow chart. Steps involved in the in vitro reconstitution of 30S subunits using the DnaK chaperone system and possible modes of analysis are given in a sequential manner.

After this purification scheme, the recovered particles were ready for further analysis, some of which are suggested in FIG. 6. The importance of particle purification was demonstrated in three independent studies. First, Alix et al. (2003) attempted to assess the functionality of DnaK chaperone system formed 30S subunits by traditional polyphenylalanine synthesis assay (utilizing S150 extract). Surprisingly, they did not observe an increase in activity over low temperature reconstitutions in the absence of chaperone. However, in these experiments the reconstitutions were directly tested for activity, i.e., the crude chaperone-containing reconstitution reactions were added directly to the functional assay with no steps taken to purify the ribosomal particle. Similar results were observed when poly(U)-dependent tRNA binding with crude chaperone-containing reconstitution mixtures was attempted (unpublished results). Therefore, it has been suggested that DnaK chaperone system components, which remain bound to the 30S particles, diminish the functional capacity of these particles. Indeed, it has been demonstrated that DnaK can remain bound to the 30S particles even through the course of sucrose gradient sedimentation (Maki et al., 2003). It would seem that the binding of the chaperones to the 30S particles is quite robust at low temperatures. Therefore, these purification steps are important to "reveal" the functional nature of 30S subunits that are formed in the presence of these factors under these otherwise non-permissive conditions. Also, it should be noted that selection of an appropriate assay is critical for monitoring changes in function. For example, while peptide bond formation is a rigorous test of ribosome function, it may not be ideal for monitoring 30S subunit function, as it has been suggested that association with 50S subunits might mask defects in 30S subunits (Maki et al., 2003; Huang et al., 2003).

Discussion

The minimal system utilized in *E. Coli* small ribosomal subunit reconstitution allows detailed probing and experimentation to gain an understanding of 30S ribosomal subunit assembly. Also, the temperature-sensitive nature of the 30S subunit in vitro reconstitution (Held et al., 1975) can be used as a means to identify assembly factors that facilitate 30S subunit assembly under otherwise non-permissive conditions (Maki et al., 2002). Initial investigations using this approach have revealed a role for the DnaK chaperone system in 30S subunit assembly (Maki et al., 2002; Maki et al., 2003) (FIG. 5). The extensive purification that is required to observe function from the chaperone-assembled subunits suggests that there are additional factors that work in concert during this step of 30S subunit assembly, e.g., RimJ. Indeed, genetic studies have implicated many factors in 30S and 50S ribosomal subunit assembly (see Alix et al., 1993; Bylund et al., 1998; Dammel et al., 1993; Dammel et al., 1965; El Hage et al., 200-1; Inoul et al., 2003; Jones et al., 1996; Ruggen et al., 1998; Sbai et al, 1998; Toone et al., 1991; Xia et al., 1993, for examples). Given that dnaK is not essential for viability in *E.* coli (Paek and Walker, 1987) and recent findings (see Example VI), identification of additional 30S subunit assembly factors is highly likely.

One difference between the minimal in vitro ribosome assembly system described herein and in vivo ribosome formation is that in bacteria, ribosome assembly occurs as the rRNA is being synthesized and modified. Thus, the fully mature rRNAs that are generally used in the reconstitutions experiments obviate many steps that occur in vivo. However, it has been demonstrated that in vitro transcribed rRNA, lacking modifications, can participate in reconstitution of functional particles (Krzyzosiak et al., 1988; Green et al., 1999; Khaitovich et al., 1999). The evidence gathered to date indicates that rRNA modifications are not required for baseline functioning of ribosomes (Krzyzosiak et al., 1988; Green et al., 1999; Khaitovich et al., 1999), but they are well correlated with functional sites within the ribosome (see Decatur et al., 2002). These findings suggest that the modifications may play a significant role in vivo, perhaps during particle assembly or function. These modifications may be beneficial when cells are challenged and growth conditions are not ideal.

A similar biochemical approach to the one described herein should be useful identification of 50S ribosomal subunit assembly factors. The procedure for in vitro reconstitution of functional 50S subunits using natural ribosomal components is more complicated than that for functional 30S subunits (Nomura et al., 1969; Nomura et al., 1970; Nierhaus et al., 1974). A complete set of recombinant E. coli 50S subunit proteins has now been produced (Semrad et al., 2004) and those are useful to prepare 50S subunits and also to identify factors directly involved in assembly. Moreover, the reconstitution of both subunits from recombinant components, and the subsequent formation of a fully functional 70S ribosome in vitro from non-natural components, would allow for an essentially "cell-free" ribosome.

For many years, details of eukaryotic ribosome assembly appeared to lag behind those of prokaryotic ribosomes due to lack of an in vitro system. However, many recent studies have begun to reveal the complexity of eukaryotic ribosome biosynthesis (Tschochner et al., 2003; Fromont-Racine et al., 2003). The identification of eukaryotic assembly factors and a better understanding of the role of RNA synthesis and modification in ribosome biogenesis may allow for an in vitro reconstitution system for eukaryotic ribosomes. However, the compartmentalization of different steps of eukaryotic ribosome biogenesis in the nucleolus, nucleoplasm and cytoplasm suggest that in vitro reconstitution of functional eukaryotic ribosomes may be more complicated. Nevertheless, the procedures detailed herein may be of use for not only studying 30S subunit assembly but also assembly of the 50S subunit, 70S ribosome and perhaps other large macromolecular machines.

EXAMPLE V

Materials and Methods

In Vitro Reconstitution, Sucrose Gradient Purification, and Western Blot Analysis In vitro reconstitution and sucrose gradient purification of particles was performed as described by Culver et al. (1999; 2000). In all reconstitution experiments, the final buffer concentration was 80 mM K$^+$-Hepes pH 7.6, 20 mM MgCl$_2$, 330 mM KCl, and 0.01% Nikkol. The concentration of 16S rRNA was 0.4 µM, while the chaperone components were present at concentrations of: 0.4 µM DnaK and DnaJ, 0.8 µM GrpE, and 1 mM ATP unless otherwise noted. TP30 concentration was at 1.6 µM or 2 µM (for all reported results except those in the last paragraph under "Results"). Recombinant proteins were present at a concentration of 3.6 µM (for results reported in the last paragraph under "Results"). The concentrations used are based on optimization experiments for individual protein preparations.

For TP30 experiments, 16S rRNA was heated at 42° C. for 20 minutes, and then cooled on ice for 15 minutes. TP30 and chaperone components were added, and the particles were incubated at 15° C. for 2 hours. Particles were then subjected to sucrose gradient sedimentation as described in Maki et al. (2002). The particles were collected from gradients, and absorbance readings at 260 nm were taken. Equal amounts according to RNA absorbance were directly precipitated with ethanol (2.5×) or equal amounts were loaded on Centricon 100s (Amicon, Millipore Corp. Bedford, Mass.). Particles were concentrated then washed twice with 2.5 ml of Protein Storage Buffer (PSB; 1 M KCl, 20 mM MgCl$_2$, and 80 mM K$^+$-Hepes pH 7.6), prior to being ethanol precipitated. Western Blot analysis was then performed as described in Maki et al. (2002).

In the recombinant protein experiment, 16S rRNA was heated at 42° C. for 20 minutes, and then cooled on ice for 15 minutes. Primary binding proteins were then added and incubated 20 minutes on ice. Secondary binding proteins were added, and particles were again subjected to a 20 minute incubation on ice. Chaperone components were added and particles were incubated at 15° C. for 30 minutes. After sucrose gradient purification, equal amounts (according to OD$_{260}$) were loaded on centricon 100s and particles were treated as described above. Tricine SDS PAGE (Schagger et al., 1987) and silver-staining (Marshall, 1984) were then performed.

Anti-DnaK, -GrpE, -DnaJ, and secondary antibodies were from StressGen (Victoria, BC, Canada). The ECL western blot analysis kit was purchased from Amersham-Pharmacia (Piscataway, N.J.) and used as directed.

DnaK Affinity Chromatography and Analysis

ER2566 cells in which chitin-binding domain tagged DnaK had been overexpressed (Maki et al., 2002) were resuspended in a magnesium-free buffer (330 mM KCl, 20 mM K$^+$ Hepes 7.6, 2.5 mM EDTA, 6 mM BME). The cells were then sonicated and the resulting supernatant was loaded on a 3-ml chitin column pre-equilibrated in the same buffer. The column was then washed with two column volumes of this buffer. All of the following column washes were performed with buffers that include the components listed above but also 10 mM MgCl$_2$ and increasing amounts of KCl: one column volume each at 500 mM KCl, 750 mM KCl, and 1 M KCl. ATP was then added to a concentration of 100 µM, and the column was rocked in the cold room for 30 minutes. The flow-through was collected, and the column was washed with one column volume of 1 M KCl. Finally, the DnaK was cleaved from the column with 40 mM DTT overnight and then collected. RNA was extracted from samples as described in Culver et al.

(2000) for native gel electrophoresis on a Tris composite gel (Dahlberg and Peacock, 1971) and primer extension (Merryman et al., 1998; Moazed et al., 1986), whereas western analysis was performed on the samples after ethanol precipitation (see above).

Tris Composite Gel

The Tris composite gel was 3% acrylamide (37.5:1), 1×TBE, and 0.5% agarose.

Results

To understand the interaction of the DnaK chaperone system with assembling 30S subunits, in vitro reconstitution was performed with purified chaperone components. In this manner, the relationship between assembling 30S subunits and DnaK, DnaJ and GrpE was assessed. These studies were pursued to determine if and how the DnaK chaperone system components interact with 30S subunit intermediates and whether the chaperone system was working in a manner similar to that observed in its protein-folding role. Previous work demonstrated the importance of purification of chaperone-treated 30S subunit intermediates for analysis (Alix et al., 2003; Maki et al., 2002; Maki et al., 2003). Purification of intermediate particles via sucrose gradient sedimentation coupled with semi-quantitative western blot analysis was employed to monitor association of chaperone components with in vitro formed 30S intermediates under various conditions. This allows association of chaperone components with the pre-30S subunits to be assessed but does not allow binding constants to be determined. In brief, 16S rRNA, TP30 and chaperone components were incubated together at 15° C., sucrose-gradient purified, equalized according to RNA content, and subjected to subsequent analysis.

DnaJ/30S Intermediate Interactions

In protein folding, DnaJ recruits substrate to DnaK and accelerates the rate of ATP hydrolysis to lock the DnaK in the DnaK-ADP-substrate conformation (Wittung-Stafshede). It has been shown that DnaJ (in the context of S100 extract) did not stably associate with small subunit assembly intermediates (Maki et al., 2002). However, DnaJ was present in the extract and thus could assume a more transient association as observed in the protein folding cycle. Here, using a purified set of chaperone components, DnaJ association with assembly intermediates can be observed under various conditions. In the absence of other components, DnaJ is found associated with the intermediate RNP both in the presence and absence of ATP. When both DnaK and DnaJ are added to the intermediate particle, association of DnaJ is observed again in the presence or absence of ATP. However, in the presence of the complete chaperone system, the addition of ATP appears to have an effect on DnaJ association. Association of DnaJ with the intermediate is observed in the presence of DnaK and GrpE, without added ATP. However, in the presence of ATP, significantly less DnaJ is found associated with the assembly intermediate. These results are slightly different from those observed using S100 extract (Maki et al., 2002) and suggest that in high functional concentrations and in the absence of competition from extract components, DnaJ can indeed be found associated with 30S subunit intermediates. However, under the conditions that are most permissive for 30S subunit assembly, the abundance of DnaJ associated with the intermediate is reduced. These results suggest that DnaJ may play a role in pre-binding the intermediate and aiding in DnaK association, very much like the role of DnaJ in protein folding.

DnaK/30S Intermediate Interactions

DnaK is the central player in the hsp70 protein folding cycle. It binds hydrophobic patches of un- or misfolded proteins and facilitates their proper folding. ATP hydrolysis enables DnaK's tight binding to substrate, and the conformational change that occurs when ADP is exchanged allows it to release substrate (McCarty et al., 1995). In this study using purified components, DnaK was found associated with 30S subunit assembly intermediates under various conditions. DnaK association with the 30S intermediate RNP is observed in the presence of DnaJ and in the presence of DnaJ and GrpE. In both cases, the addition of ATP leads to a reduction in the amount of bound DnaK, with this result being most pronounced in the presence of the full-chaperone system. It was also demonstrated that DnaK binds to the pre-30S RNP in the absence of its co-chaperones either with or without ATP. Virtually no bound DnaK is detected in the presence of DnaK, GrpE and 1 mM ATP. In contrast, when DnaJ is also present, bound DnaK can be detected. One possible explanation for this observation is DnaJ-facilitated rebinding of DnaK to the assembly intermediate. Overall, these results suggest that DnaK interacts with the 30S subunit intermediate in a manner that is consistent with its interaction with protein substrates.

To further investigate the effect of ATP on DnaK binding, ATP and temperature titrations were performed on particles formed in the presence of the entire DnaK chaperone system. At 15° C., the amount of DnaK bound to assembling intermediates rapidly decreased with a corresponding increase in the concentration of ATP from 0 to 1 mM. This trend was also observed when particles were formed under these conditions but incubated at 42° C., although the initial amount of DnaK bound appeared to be much lower than that seen at 15° C., suggesting a more dynamic interaction at higher temperature. These results suggest DnaK binding to 30S subunit assembly intermediates is influenced by not only its co-chaperones but also by temperature and ATP concentration. These observations may have marked functional implications since it was previously shown that association of DnaK with 30S particles inhibits their function (Maki et al., 2003).

GrpE/30S Intermediate Interactions

GrpE's role in the protein folding cycle is aiding DnaK in nucleotide exchange and substrate release (Harrison, 2003). In this analysis, DnaK, DnaJ and GrpE were incubated with assembly intermediates at 15° C. in the presence and absence of ATP. GrpE was found associated with intermediates in the absence of ATP however the presence of ATP results in a dramatic decrease in detectable GrpE. This is consistent with GrpE's release with DnaK at the completion of a folding cycle. However, these results are slightly different than those found previously with *E. coli* S100 extract (Maki et al., 2002), where GrpE was found associated with the RNP in the presence of DnaK, DnaJ and ATP. The slight discrepancy can be attributed to the use of individually purified DnaK chaperone system components and a significantly higher concentration of ATP, resulting in more complete release of GrpE.

Generally, these results describing the DnaK chaperone system association with 30S subunit intermediates appear to be consistent with what is known about the interactions of the DnaK chaperone system components with substrates during the protein folding cycle. Although this analysis does not delve into the mechanism, the association results follow the convention of the previously elucidated roles of DnaK and its co-chaperones DnaJ and GrpE in protein folding (Bukau and Horwich, 1998). Therefore, it appears that the reaction binding cycle may be similar between protein substrates and this RNP.

DnaK Interacts with Small Subunit Ribosomal Components In Vivo

Next, a role for DnaK in 30S subunit assembly in vivo was addressed. Previous in vivo studies using a dnaK mutant allele (dnaK756) suggested that the absence of DnaK resulted in ribosome biogenesis defects in *E. coli* (Alix et al., 1993). However, these studies did not reveal a direct role in 30S subunit assembly for DnaK in vivo. In the yeast *Saccharomyces cerevisiae* (Harnpicharnchai et al., 2001), an affinity chromatographic approach using a protein shown to bind pre-ribosomal particles has proven powerful as a tool for characterizing and purifying factors that are associated with ribosomal assembly intermediates in vivo. Here a related approach was used to determine if DnaK bound 30S subunit intermediates in vivo. An inducible, tagged version of DnaK was used to allow overexpression of DnaK within wild type cells and subsequent affinity chromatography of DnaK and associated cellular components. The bound components were eluted by a potassium chloride gradient (330 mM to 1M KCl), a high salt ATP wash, and finally removal of DnaK and bound components from the column. Initially, the resulting fractions were assayed by native gel electrophoresis for the presence of large RNAs to determine if DnaK associates with ribosomal particles in vivo. 16S rRNA was found in all samples eluted, and the amount of RNA detected varied in different samples. This observation suggests that the RNA might be present in different complexes that display differential affinity for DnaK. 23S rRNA was released with DnaK from the column. The presence of 23S rRNA with the eluted DnaK protein might be attributed to DnaK's association with the 50S subunit portion of the 70S ribosome. However, since 23S rRNA is not observed in the other fractions, association with the 50S subunit alone cannot account for the presence of 16S rRNA in various column fractions. These results indicate that DnaK indeed interacts with rRNA in vivo.

Given that DnaK appears to be associating with precursor 30S subunits in vitro, it was investigated whether the 16S rRNA associated with DnaK in vivo is mature at its 5' end. Primer extension analysis was used to determine the extent of 16S rRNA processing. In all lanes, the 5' end of the 16S rRNA can be clearly seen as a very strong band in the primer extension gel. Interestingly, an unusually large proportion of pre-cursor 16S rRNA was also observed in the samples eluted from the column as compared with a control extension. Very little unprocessed 16S rRNA was observed in the control 16S rRNA isolated from wild type 30S subunits. When the amount of precursor 16S rRNA is expressed as a ratio of precursor to processed 16S rRNA, the ratio for control unmodified 16S rRNA is only 0.01, whereas fractions eluted from the DnaK affinity column range from 0.15 to 0.38. The presence of 16S rRNA with a pre-5' end suggests that DnaK is interacting in vivo with immature 16S rRNA, possibly in the context of the 30S subunit precursor.

To assess whether small subunit ribosomal proteins are also found associated with DnaK in vivo, elution of S4 and S3 from the DnaK column was monitored. In the absence of RNA, these proteins were previously shown to bind a DnaK column with different affinities. These proteins were also chosen because of their different properties in 30S subunit assembly. S4 is a primary binding protein, and thus can be expected in early stage assembling small subunits, while S3 is a tertiary binding protein and will be present only near the end of 30S subunit assembly. S3 was found in earlier eluting fractions, while S4 was detected in both early and late fractions. The presence of S4 in the later eluting fractions, where S3 is absent, raises the possibility that DnaK is associating with partially assembled 30S subunits. This would indicate a role for DnaK in 30S subunit assembly in vivo. This assertion is consistent with data using a mutant allele of dnaK where under non-permissive conditions, 30S subunit assembly is impaired (Alix et al., 1993). Taken together, these affinity chromatography results suggest that DnaK may interact with 30S subunit precursors in vivo, as premature 16S rRNA and small subunit ribosomal proteins are co-eluting from the DnaK column. Also, it appears that DnaK could have altered affinity for more mature 30S subunits than for early assembly intermediates, suggesting differential interaction with these particles.

DnaK Chaperone System Components Stabilize Assembly Intermediates

While the work presented here indicates that the DnaK chaperone system, and most notably DnaK itself, interacts with 30S subunit assembly intermediates, the consequences of such interactions are still not well understood. It has been observed that in vitro-formed RI particles are unstable (Held et al., 1973; Maki et al., 2002). However, the heat-activated form of this intermediate, RI* appears to be more stable. Thus, this stabilization of the intermediate can be used to monitor a transition during 30S subunit assembly and to determine if the DnaK chaperone system stabilizes the RI particle in a manner similar to heat treatment. RI particles were formed and their stability was tested using different heat and chaperone conditions. As expected, the protein complement of RI is reduced relative to that observed for heat-formed RI*($\Delta$RI*). The protein complement of the particles treated at low temperature with DnaK alone or DnaK and ATP more closely resembles that of $\Delta$RI*, suggesting DnaK or DnaK and ATP are capable of stabilizing the RNP in a manner analogous to heat treatment. Due to the small and similar size (approximately 10-23 kDa) of primary and secondary binding proteins, resolution of the individual proteins by SDS-PAGE is not ideal. However, S4 and S7, two of the largest components of RI and RI* can be resolved relatively easily and are prominent in $\Delta$RI* and in the DnaK treated particles. The stabilization of pre-30S particle by DnaK could be a crucial part of the mechanism by which 30S subunits are assembled under otherwise non-permissive conditions. Stabilizing properly folded intermediates could increase the overall efficiency of 30S subunit formation, thus suggesting a significant role for DnaK in this process.

Discussion

Utilizing a variety of techniques including semi-quantitative western blot analysis, primer extension, affinity chromatography and stability assays, the interactions of the DnaK chaperone system components and the forming 30S subunit of the E. coli ribosome were analyzed. The E. coli hsp70 chaperone system components were all observed to interact with pre-30S particles and the interactions appear, at least at this level of analysis, to be similar to those observed between the chaperone components and protein folding substrates. This suggests that there may be similarities between the mechanism by which DnaK folds proteins and facilitates 30S subunit assembly. Additionally, data was presented that suggests DnaK can act to stabilize 30S subunit intermediates and associate with pre-30S particles in vivo. These findings suggest a significant role for the DnaK chaperone system in 30S subunit formation.

For the first time, DnaJ was found associated with 30S subunit assembly intermediates in the presence and absence of DnaK and ATP. However, in the presence of DnaK, GrpE and ATP, less DnaJ was associated with the assembly intermediate. These results are consistent with previous data (Maki et al., 2002); when crude E. coli extract (S100) was used, DnaJ was not found associated with the RNP. Under these conditions, all of the chaperone components and ATP were present and thus no DnaJ association was detected. DnaK was found to bind 30S assembly RNPs in the presence of DnaJ or DnaJ and GrpE. Under both conditions, the amount of bound DnaK detected decreased in the presence of ATP. Virtually no DnaK was observed in association with the assembly intermediate when DnaJ, GrpE and ATP were present as well. Also, the amount of DnaK bound to the pre-30S RNP was decreased by both increased temperature and concentration of ATP. Finally, GrpE bound the RNP in the presence of DnaK and DnaJ, but its association was greatly reduced in the presence of ATP. These results demonstrate that all of the DnaK chaperone system components are capable of interacting with 30S subunit assembly intermediates and that the observed interactions follow a pattern that is reminiscent of the interaction of these same components when folding protein substrates.

DnaK has been shown to interact with 70S ribosomes and to play a role in ribosome assembly in vivo (Alix et al., 1993; Alix et al., 2003). In recent work (Hage et al., 2004), the DnaK chaperone system was found to facilitate the assembly of in vivo formed 21S(RI) intermediates. Additional in vivo work has shown that overexpression of small subunit ribosomal proteins S4 and S8 can rescue the temperature sensitive phenotype of the mutant dnaK allele, dnaK756 (Maki et al., 2002). In the studies presented here, DnaK's in vivo interaction with 30S subunit components was explored utilizing affinity chromatography coupled with native gel electrophoresis, primer extension, and western blot analysis. Affinity chromatography of tagged DnaK revealed that pre-16S rRNA, the primary binding protein S4, and to a significantly less extent tertiary binding protein S3, associate with DnaK in vivo. These data raise the intriguing possibility that DnaK may assist in the early stages of 30S subunit assembly in vivo. It is possible that DnaK could be recruiting primary binding proteins (such as S4) that bind near the 5' end of 16S rRNA early in assembly. Additionally, the involvement of precursor 16S rRNA with DnaK hints at the possibility of co-transcriptional formation of the 30S subunit in vivo, a likelihood that has generated much interest.

The temptation might be to speculate that DnaK is interacting with ribosomal small subunit proteins simply by virtue of DnaK binding regions within these proteins. However, when an algorithm designed to predict DnaK binding sites (Rudiger et al., 1997) was used, none of the ribosomal proteins were identified as ideal DnaK substrates (unpublished results). However, this should not come as a surprise, as the characteristic DnaK binding region is hydrophobic, and none of the small subunit ribosomal proteins are overly hydrophobic. The interaction of chaperones with RNA is not as prevalent in the literature as their interaction with proteins, but it is not unprecedented. For example, DnaK has been shown to interact with 5S rRNA by Northwestern analysis (Okada et al., 2000). Zimmer and colleagues propose that chaperones may assist in RNA folding and demonstrated that human hsp70's RNA binding activity is influenced by its co-chaperones (Zimmer et al., 2001). Additionally, GroEL (a chaperonin) has been implicated in 9S rRNA processing, perhaps via regulation of RNase E (Sohlberg et al., 1993). Thus it would not be unprecedented if DnaK interacted with 16S rRNA as part of the 30S subunit intermediate RNP and not just with individual ribosomal small subunit proteins or 16S rRNA.

The stabilization of 30S-subunit assembly intermediates by the DnaK chaperone system suggests that DnaK facilitates 30S subunit assembly in this manner. RI particles are inherently unstable, but when heat-treated, they form RI*, a particle that sediments at 26S, exhibits increased stability, and is competent for further assembly into functional 30S subunits. Using sucrose gradient sedimentation, molecular sieving filters, and SDS-PAGE, this stabilization, previously only observed with heat treatment at 42° C., was achieved at low temperature with DnaK or the entire DnaK chaperone system (data not shown). Thus it appears that DnaK is acting at this stage of 30S subunit assembly.

These results suggest that through recruitment of the proper components and stabilization of assembly intermediates, the DnaK chaperone system is able to assist in the assembly of 30 subunits. It appears that the DnaK components may interact with not only small subunit proteins, but also the 16S rRNA containing RNPs in this function. The in vivo binding of precursor 16S rRNA in this context also brings up the intriguing possibility that the DnaK chaperone system could aid in the co-transcriptional assembly of ribosomal small subunits in vivo.

EXAMPLE VI

Modification Interference Mapping of Specific 16S rRNA Residues Involved in Assembly To gain an understanding of which nucleotides are important for the RI to RI* transition and 30S subunit formation, modification interference is employed. Modification interference has proven highly successful in determining nucleotides that are critical for nucleic acid function, structure and interactions (Conway et al., 1989; Siebenlist et al., 1980). Also, the validity of this approach for identifying sites of RNA/protein interactions has been confirmed by structural studies (Bartel et al., 1991; Battiste et al., 1995; Kjems et al., 1992; Pritchard et al., 1994; Puglisi et al., 1992; Tao and Frankel, 1992; Weeks et al., 1990). Modification interference has been used to define, more precisely than standard footprinting experiments, residues in 30S subunits that are important for tRNA binding (von Ahsen and Noller, 1995).

A key to successful modification interference analysis is the ability to distinguish modified products, which are functional, from their non-functional counterparts. Pre-30S particles are chemically modified, allowed to assemble and then stalled assembly intermediates are differentiated from 30S subunits by tRNA binding using biotinylated tRNA (Promega) and streptavadin magnetic beads. Since nucleotides important for tRNA binding have already been identified using this approach (von Ahsen and Noller, 1995), the functional selection will not bias the interpretation, as the diminution of these modified residues is anticipated from the selected pool. For all of these experiments, previous r-protein footprinting (see Powers and Noller, 1995) and 30S subunit structural data (Brodersen et al., 2002) can be used to differentiate between modifications that block r-protein association from those that restrict or alter conformational changes within 16S rRNA during the course of 30S subunit assembly.

A second consideration for experiments to define the nucleotides in rRNA that are important for the RI to RI* transition, is the modification reaction itself. The intermediate particles are subjected to limited chemical modification, such that a portion of the population retains its ability to form 30S subunits. All of the base-specific probes that are used [1-cyclohexyl-3-(2-morpholinoethyl) carbodiimide metho-p-toluene sulfonate (CMCT), diethyl pyrocarbonate (DEPC), dimethyl sulfate (DMS), and kethoxal] can react with RNA and be quenched, at low temperature, thereby allowing a variety of intermediates and conditions to be sampled.

For these experiments, 16S rRNA and r-proteins (either recombinant or natural in the form of TP30) are incubated under reconstitution conditions but at low temperature (0°-15° C.) to stall assembly at RI. After modification and quenching, the particles are incubated at elevated temperature (42° C.) allowing assembly to proceed and then tRNA binding selection is performed. Primer extension analysis of the total modified pool compared to the selected population can reveal sites of modification that restrict 30S subunit assembly and thus reveal nucleotides that are integral to this process.

In addition to modifying 16S rRNA-within the RI intermediate, other stages of assembly can also be evaluated using modification interference. RI* could also be modified to allow dissection of later events in 30S subunit assembly. For these experiments, a sub-set of recombinant small subunit r-proteins are used so that RI* can be formed by incubation at elevated temperature without full assembly occurring. Once RI* has been modified, the remaining r-proteins can be added and assembly can proceed. These experiments, coupled with those described above, can distinguish between nucleotides that are important for the RI to RI* transition and those that are critical for the conversion of RI* to 30S subunits. To identify nucleotides involved in early assembly events for which there is a significant dearth of data, naked 16S rRNA is modified prior to addition of the r-proteins and then subsequent 30S subunit assembly. Altering the step of reconstitution, by staged r-protein addition and changes in temperature, when modification is performed allows investigation of many different stages of assembly.

EXAMPLE VII tRNA Binding as a Monitor of Factor-Dependent 30S Subunit Assembly

To monitor factor-dependent 30S assembly at low temperature, tRNA binding may be employed as 30S subunits were determined to bind tRNA at 15° C. nearly as well as at 37° C. Thus, this assay can be used to monitor the facilitated conversion of stalled intermediates to functional 30S subunit. The use of this assay, in lieu of sucrose gradient sedimentation, has multiple advantages including the speed of the assay and the ease with which multiple samples can be simultaneously examined (tRNA binding takes about 8 hours to analyze 60 samples; sucrose gradient sedimentation requires about 18 hours to analyze 12 samples). Perhaps the biggest advantage is that by monitoring tRNA binding, quantitative analysis and specific activity calculations can readily be performed during factor identification.

The tRNA binding approach was evaluated using two alternative post-ribosomal wild-type *E. coli* extracts. Although both extracts have a background level of tRNA binding, there was an increase in tRNA binding of either 44% or 86% (for the two extracts, respectively) in the presence of stalled reconstitutions. Virtually no tRNA binding is observed from stalled intermediates alone (Maki et al., 2002). Assembly factors are differentiated from mere tRNA binding proteins by assaying fractions in the presence and absence of stalled intermediates; fractions that only have activity in the presence of the intermediate represent the assembly factors and are further analyzed. These control assays are used through various purification steps until the pool of factors has been deconvoluted. It should be noted that DnaK is present in these extracts yet functional 30S subunit formation can be observed. Given the findings that, when purified chaperone components are added to the low temperature reconstitutions, DnaK remains bound to the 30S particles (Maki et al., 2002), these results suggest that additional factors are present in these wild-type extracts. These factors could aid in release of DnaK from the assembly particle, or alternatively, these factors could act in lieu of DnaK. Either possibility indicates that additional factors are present in wild-type extracts.

In addition to using wild-type extracts, it is likely that extracts prepared from specific *E. coli* mutant strains are valuable in the identification of extra-ribosomal assembly factors. The surprising ability of *E. coli* to grow in the absence of the primary binding protein S15, contrary to all the suggestions from in vitro experiments, led to the speculation that in the ΔrpsO background additional factors may compensate for the loss of this protein. Extracts prepared from this strain are compared with those from its parental strain to assess whether there is any difference in augmentation of 30S subunit assembly, i.e., if in response to deletion of S15 an assembly factor is upregulated. Also, extracts prepared from the dnaK/dnaJ deletion strain (Kang and Craig, 1990) should also allow detection of additional assembly factors whose activities might be masked in the presence of the DnaK chaperone system. Indeed, incubation of stalled intermediates with extract prepared from the dnaK/dnaJ deletion strain results in measurable, although reduced compared to wild-type (20% of wild-type) activation in tRNA binding capacity. These results suggest that DnaK is playing a role in activation of assembly in the extract milieu but that additional factors can also be detected.

In vitro experiments indicate that r-protein S16 alters the rate of 30S subunit formation (Held and Nomura, 1975). Data suggests that the rate of in vitro reconstitution of 30S subunits in the absence of S16 can be enhanced by the presence of exogenous components (data not shown). Extract-dependent changes in the rate of functional 30S formation are analyzed in the absence of S16 by monitoring tRNA binding. Factor(s) responsible for this activation are purified and characterized. This system enables the assay of factor function at 37° C. (bypassing the low temperature incubation associated with RI activation). This approach is of great interest as it offers the possibility of detecting factors that act at steps other than the RI to RI* transition and may facilitate identification and characterization of factors, thereby complementing other approaches.

To determine the complexity of the stimulatory effects and to identify factor(s) responsible for facilitating 30S subunit assembly, extract fractionation is employed. DEAE-cellulose is one choice for a column matrix, and extracts are fractionated using a linear salt gradient. Fractions are then assayed for reconstitution-dependent activation of tRNA binding. The complexity of the functional fractions is determined via SDS-PAGE and mass spectrometry (MS). The specific activity of the fractions as a monitor of purification is followed. If there is a precipitous decrease in specific activity, the requirements for co-factors or for multiple components may be addressed by fraction doping.

REFERENCES

Agalarov et al., *Eur. J. Biochem.*, 266:533 (1999).
Agalarov et al., *Proc. Natl. Acad. Sci. USA* 95:999 (1998).
Agashe et al., Cell Dev. Biol., 11:15 (2000).
Agashe et al., *Semin. Cell Dev. Biol.*, 11:15 (2000).
Alix et al., *Proc. Natl. Acad. Sci. USA* 90:9725 (1993).
Alix et al., *RNA*, 9:787 (2003).
Bartel et al., *Cell*, 67:529 (1991).
Battiste et al., *J. Biomol. NMR*, 6:375 (1995).
Brodersen et al., *J. Mol. Biol.*, 316:725 (2001).
Bukau et al., *Cell*, 92:351 (1998).
Burston et al, *Essays Biochem.* 29:125 (1995).
Bylund et al., *J. Bacteriol.*, 180:73 (1998).
Cannone et al., *BioMed Central Bioinformatics*, 3:2 (2002).
Carson, *Methods Enzymol.*, 277:493 (1997)
Charollais et al., *Mol. Microbiol.*, 48:1253 (2003).
Conway et al., *Methods Enzymol.*, 180:369 (1989).
Culver et al., *J. Mol. Biol.*, 286:355 (1999).
Culver et al., *Methods Enzymol.*, 318:446 (2000).
Culver et al., *RNA*, 4:1471 (1998).
Culver et al., *RNA*, 5:832 (1999).
Cumberlidge et al., *J. Mol. Biol.*, 131:169 (1979).
Dahlberg et al., *J. Mol. Biol.*, 55:61 (1971).

Dammel et al., *Genes Dev.*, 7:660 (1993).
Dammel et al., *Genes Dev.*, 9:626 (1995).
Decatur et al., *Trends Biochem. Sci.*, 27:344 (2002).
Dekker et al., *J. Mol. Biol.*, 270:321 (1997).
DeRiemer et al., *J. Labeled Compd. Radiopharm.*, 18:1517 (1981).
Dohme et al., *Proc. Natl. Acad. Sci. USA*, 73:2221 (1976).
El Hage et al., *Mol. Gen. Genet.* 264: 796 (2001).
Fink, *Physiol. Rev.*, 79:425 (1999).
Franceschi et al., *J. Biol. Chem.*, 265:16676 (1990).
Fromont-Racine et al., *Gene*, 313:17 (2003).
Georgopoulos et al., *Mol. Gen. Genet.*, 172:143 (1973).
Geyl et al., *Mol. Gen. Genet.*, 181:309 (1981).
Giri et al., *Adv Protein Chem.*, 36:1 (1984).
Graifer et al., *Biochim. Biophys. Acta*, 1008:146 (1989).
Green et al., *Biochem.*, 38:1772 (1999).
Green et al., *RNA*, 2:1011 (1996).
Grondek et al., *RNA*, 10:1861 (2004).
Guthrie et al., *Proc. Natl. Acad. Sci. USA*, 63:384 (1969).
Hage et al., *Mol. Microbiol.*, 51:189 (2004).
Hardy et al., *Biochemistry*, 8:2897 (1969).
Harnpicharnchai et al., *Mol. Cell*, 8:505 (2001).
Harrison, *Cell Stress Chaperones*, 8:218 (2003).
Heilek et al., *Proc. Natl. Acad. Sci. USA*, 92:1113 (1995).
Heilek et al., *RNA.*, 2:597 (1996a).
Heilek et al., *Science* 272:1659 (1996b).
Held et al., *Biochemistry*, 12:3273 (1973).
Held et al., *J. Biol. Chem.*, 248:5720 (1973).
Held et al., *J. Biol. Chem.*, 249:3103 (1974).
Held et al., *J. Biol. Chem.*, 250:3179 (1975).
Herold et al., *Mol. Gen. Genet.*, 203:281 (1986).
Huang et al., *J. Mol. Biol.*, 327:521 (2003).
Inoue et al., *Mol. Microbiol.*, 48:1005 (2003).
Isono et al., *Mol. Gen. Genet.*, 177:645 (1980).
Jones et al., *Mol. Microbiol.*, 21:1207 (1996).
Kaltschmidt et al., *Proc. Natl. Acad. Sci. USA*, 67:1276 (1970).
Kaltschmidt, *Anal. Biochem.*, 43:25 (1971).
Kang et al., *J. Bacteriol.*, 172:2055 (1990).
Kellogg et al., *Mol. Biol. Cell*, 3:1 (1992).
Khaitovich et al., *Biochem.*, 38:1780 (1999).
Khaitovich et al., *Biochemistry*, 38:1780 (1999).
Khaitovich et al., *J. Mol. Biol.*, 291:1025 (1999).
Kjems et al., *EMBO. J.*, 11:1119 (1992).
Kowalak et al., *Protein Sci.*, 5:1625 (1996).
Krzyzosiak et al., *Anal. Biochem.*, 175:373 (1988).
Krzyzosiak et al., *Biochem.*, 26:2353 (1987).
Laemmli, *Nature*, 227:680 (1970).
Leibowitz et al., *Proc. Natl. Acad. Sci. USA*, 68:1866 (1971).
Liberek et al., *Proc. Natl. Acad. Sci. USA* 88:2874 (1991).
Lill et al., *Biochemistry*, 25:3245 (1986).
Lindahl, *J. Mol. Biol.*, 92:15 (1975).
Maki et al., *Mol Cell.*, 10:129 (2002).
Maki et al., *RNA*, 9:1418 (2003).
Marshall, *Anal. Biochem.*, 136:340 (1984).
Matsudaira, *J. Biol. Chem.*, 262:10035 (1987).
McCarty et al., *J. Mol. Biol.* 249:126 (1998).
Merryman et al., In: RNA: Protein Interactions. A Practical Approach. Smith (ed), New York, N.Y., Oxford Univ. Press, pp. 237-253 (1998).
Milligan et al., *Nucleic Acids Res.*, 15:8783 (1987).
Mizushima et al., *Nature*, 226:1214 (1970).
Moazed et al., *Cell* 47:985 (1986).
Moazed et al., *J. Mol. Biol.*, 187:399 (1986).
Nashimoto et al., *J. Mol. Biol.*, 62:121 (1971).
Nierhaus et al., *J. Mol. Biol.*, 74:587 (1973).
Nierhaus et al., *Proc. Natl. Acad. Sci. USA*, 71:4713 (1974).
Nierhaus, In Ribosomes and protein synthesis: A practical approach (ed. G. Spedding), pp. 161-189. IRL Press, Oxford University Press, Oxford, UK (1990).
Nierhaus, Reconstitution of ribosomes, In: Spedding G, ed. Oxford: Oxford University Press, pp 161 (1990).
Nirenberg et al., *Science*, 145:1399 (1964).
Noller et al., *Science*, 212:403 (1981).
Nomura et al., *Nature*, 228:744 (1970).
Nomura et al., *Quant. Biol.*, 34:49 (1969).
Okada et al., *FEBS Lett.*, 485:153 (2000).
Paek et al., *J. Bact.*, 69:283 (1987).
Powers et al., *J. Mol. Biol.*, 232:362 (1993).
Powers et al., *RNA*, 1:194 (1995).
Pritchard et al., *Nucleic Acids Res.*, 22:2592 (1994).
Puglisi et al., *Science*, 257:76 (1992).
Ramakrishnan et al., *Curr. Opin. Struct. Biol.*, 11:144 (2001).
Ramakrishnan et al., *J. Biol. Chem.*, 261:15049 (1986).
Reeh et al., *Mol. Gen. Genet.*, 173:183 (1979).
Röhl et al., *Proc. Natl. Acad. Sci. USA* 79:729 (1982).
Rudiger et al., *EMBO J.* 16:1501 (1997).
Ruggero et al., *EMBO J.*, 17:3471 (1998).
Samaha et al., *Proc. Natl. Acad. Sci. USA*, 91:7884 (1994).
Sampson et al., *Science* 243:1363 (1989).
Sbai et al., *Mol. Gen. Genet.*, 260:199 (1998).
Schagger et al., *Anal. Biochem.* 166:368 (1987).
Schaup et al., *Mol. Gen. Genet.*, 112:1 (1971).
Schmid et al., *Science*, 263:971 (1994).
Schonfeld et al., *J. Biol. Chem.*, 270:2183 (1995).
Seiber et al., *Biochemistry*, 17:3505 (1978).
Semrad et al., *RNA*, 10:1855 (2004).
Siebenlist et al., *Proc. Natl. Sci. USA*, 77:122 (1980).
Siegmann et al., *Methods Enzymol.*, 146:362 (1987).
Sohlberg et al., *PNAS USA*, 90:277 (1993).
Sorensen et al., *J. Mol. Biol.*, 281:561 (1998).
Southworth et al., *J. Mol. Biol.*, 324:611 (2002).
Stem et al., *Methods Enzymol.*, 164:481 (1988).
Studier et al., *Methods Enzymol.*, 185:60 (1990).
Tao et al., *Proc. Natl. Sci. USA*, 89:2723 (1992).
Toone et al., *J. Bacteriol.*, 173:3291 (1991).
Traub et al., *Cold Spring Harbor Symp. Quant. Biol.*, 34:63 (1969).
Traub et al., In: Moldave K, ed., New York: Academic Press, pp 521 (1981).
Traub et al., *J. Mol. Biol.*, 40:391 (1969).
Traub et al., *Proc. Natl. Acad. Sci. USA*, 59:777 (1968).
Traub et al., *Quant. Biol.*, 34:25 (1969).
Traub et al., *RNA and Protein Synthesis*, 521 (1981).
Tschochner et al., *Trends Cell Biol.*, 13:255 (2003).
Vladimirov et al., *FEBS Lett.*, 181:367 (1985).
von Ahsen et al., *Science*, 267:234 (1995).
Wall et al., *J. Biol. Chem.*, 269:5446 (1994).
Weeks et al., *Science* 249:1281 (1990).
Weitzmann et al., *FASEB J.*, 7:177 (1993).
Williamson, *RNA*, 9:165 (2003).
Wimberly et al., *Nature*, 407:327 (2000).
Wittmann et al., *Mol. Gen. Genet.*, 111:327 (1971).
Wittung-Stafschede et al., *Biochemistry*, 42:4937 (2003).
Wu et al., *EMBO J.* 15:4806 (1996).
Xia et al., *J. Mol. Biol.*, 332:575 (2003).
Yochem et al., *Mol. Gen. Genet.*, 164:9 (1978).
Zimmer et al., *RNA*, 7:1628 (2001).

All publications, patents and patent applications are incorporated herein by reference. While in the foregoing specification this invention has been described in relation to certain preferred embodiments thereof, and many details have been set forth for purposes of illustration it will be apparent to those skilled in the art that the invention is susceptible to additional embodiments and that certain of the details described herein may be varied considerably without departing from the basic principles of the invention.

What is claimed is:

1. A method to prepare a peptide, comprising:
   a) providing a defined translation reaction mixture comprising isolated i) 30S subunits comprising small subunit ribosomal proteins and 16S rRNA, ii) 50S subunits comprising large subunit ribosomal proteins, 5S rRNA and 23S rRNA, iii) charged tRNAs for at least one amino acid, iv) RNA template for translation with at least one codon corresponding to the anticodon in the charged tRNAs, and v) one or more translation factors; and
   b) incubating the mixture so as to yield a peptide encoded by the RNA template.

2. The method of claim 1 wherein the 30S subunits have one or more recombinant small subunit ribosomal proteins.

3. The method of claim 1 wherein the 50S subunits have one or more recombinant large subunit ribosomal proteins.

4. The method of claim 1 wherein the 5S rRNA or 23S rRNA is recombinant 5S rRNA or recombinant 23S rRNA.

5. The method of claim 1 wherein the 5S rRNA or 23S rRNA is natural 5S rRNA or natural 23S rRNA.

6. The method of claim 1 wherein the 16S rRNA is natural 16S rRNA.

7. The method of claim 1 wherein the 16S rRNA is recombinant rRNA.

8. The method of claim 1 wherein the 30S subunits are prepared by contacting 16S rRNA with a first subset of small subunit ribosomal proteins to form a first ribonucleoprotein complex, and then the first ribonucleoprotein complex is contacted with a second subset of small subunit ribosomal proteins and optionally one or more accessory proteins to form a second ribonucleoprotein complex.

9. The method of claim 8 wherein the second ribonucleoprotein complex is contacted with a third subset of small subunit ribosomal proteins.

10. The method of claim 9 wherein the first subset of small subunit ribosomal proteins includes S4, S7, S8, S15, S17 and S20.

11. The method of claim 10 wherein the second subset of small subunit ribosomal proteins includes S5, S6, S9, S11, S12, S13, S16, S18, and S19.

12. The composition of claim 11 wherein the third subset of small subunit ribosomal proteins includes S2, S3, S10, S14 and S21.

13. The method of claim 9 wherein the contacting is at a temperature of less than 20° C.

14. The method of claim 9 wherein all of the small ribosomal subunit proteins are recombinant proteins.

15. The method of claim 8 wherein the first subset of small subunit ribosomal proteins includes S4, S6, S11, S15, S16, S17, S18, S20, S7, S8, S9, S13 and S19.

16. The composition of claim 15 wherein the second subset of small subunit ribosomal proteins includes S5, S12, S2, S3, S10, S14 and S21.

17. The method of claim 8 wherein the contacting is at a temperature of less than 20° C.

18. The method of claim 8 wherein all of the small ribosomal subunit proteins are recombinant proteins.

19. The method of claim 8 wherein the accessory protein is DnaK, DnaJ or GrpE.

20. The method of claim 8 wherein the accessory protein a recombinant protein.

21. The method of claim 1 wherein one of the translation factors is EF-G or EF-T.

22. The method of claim 1 further comprising GTP, ATP, phosphoenolpyruvate or pyruvate kinase, or any combination thereof.

* * * * *

UNITED STATES PATENT AND TRADEMARK OFFICE
CERTIFICATE OF CORRECTION

PATENT NO. : 7,459,290 B1
APPLICATION NO. : 11/094770
DATED : December 2, 2008
INVENTOR(S) : Culver et al.

It is certified that error appears in the above-identified patent and that said Letters Patent is hereby corrected as shown below:

On the Title Page Item (56), under "Other Publications", after "Nitta, I.," insert -- et al., --.

In column 7, line 29, after "Proteins" insert -- , --.

In column 7, line 60, delete "S5" and insert -- 5S --, therefor.

In column 9, line 31, delete "Table 1)." and insert -- Table I). --, therefor.

In column 9, line 35, before "reaction" insert -- The --.

In column 13, line 13, delete "Stem" and insert -- Stern --, therefor.

In column 15, line 57, delete "tRNAPhe" and insert -- $tRNA^{Phe}$ --, therefor.

In column 16, line 2, after "Cloning" insert -- , --.

In column 16, line 21, delete "*E. Coli*" and insert -- *E. coli* --, therefor.

In column 17, line 16, delete "$tRNA^{Phe}bound$" and insert -- $tRNA^{Phe}$ bound --, therefor.

In column 21, line 44, delete "deoxychloate" and insert -- deoxycholate --, therefor.

In column 27, line 17, delete "Ssalp" and insert -- Ssa1p --, therefor.

In column 31, line 12, delete "$\alpha$-" and insert -- $\beta$- --, therefor.

In column 32, line 54, delete "$H_2O$," and insert -- $H_2O$. --, therefor.

In column 34, line 48, delete "*E. Coli*" and insert -- *E. coli* --, therefor.

In column 34, line 65, delete "200-1;" and insert -- 2001; --, therefor.

In column 36, lines 59-63, delete "(2000) for native gel electrophoresis on a Tris composite gel (Dahlberg and Peacock, 1971) and primer extension (Merryman et al., 1998; Moazed et al., 1986), whereas western analysis was performed on the samples after ethanol precipitation." and insert the same at Col. 36, Line 58, after "Culver et al." as a continuation of the paragraph.

UNITED STATES PATENT AND TRADEMARK OFFICE
CERTIFICATE OF CORRECTION

PATENT NO. : 7,459,290 B1
APPLICATION NO. : 11/094770
DATED : December 2, 2008
INVENTOR(S) : Culver et al.

It is certified that error appears in the above-identified patent and that said Letters Patent is hereby corrected as shown below:

In column 36, line 67, delete "1xTBE," and insert -- 1X TBE, --, therefor.

In column 38, line 3, delete "full-chaperone" and insert -- full chaperone --, therefor.

In column 41, line 53, delete "30S-subunit" and insert -- 30S subunit --, therefor.

In column 42, line 66, delete "rRNA-within" and insert -- rRNA within --, therefor.

In column 46, line 36, delete "Stem" and insert -- Stern --, therefor.

In column 48, line 10, in Claim 12, delete "composition" and insert -- method --, therefor.

In column 48, line 20, in Claim 16, delete "composition" and insert -- method --, therefor.

In column 48, line 29, in Claim 20, delete "protein a" and insert -- protein is a --, therefor.

Signed and Sealed this

Thirty-first Day of March, 2009

JOHN DOLL
*Acting Director of the United States Patent and Trademark Office*